US009499419B2

(12) United States Patent
de Rijk

(10) Patent No.: US 9,499,419 B2
(45) Date of Patent: *Nov. 22, 2016

(54) METHODS AND COMPOSITIONS FOR TREATMENT OF SKIN

(75) Inventor: Jan de Rijk, Veenendaal (NL)

(73) Assignee: Special Waters Patents B.V., Veenedaal (NL)

( * ) Notice: Subject to any disclaimer, the term of this patent is extended or adjusted under 35 U.S.C. 154(b) by 159 days.

This patent is subject to a terminal disclaimer.

(21) Appl. No.: 11/912,839

(22) PCT Filed: Aug. 4, 2006

(86) PCT No.: PCT/IB2006/004122
§ 371 (c)(1),
(2), (4) Date: May 21, 2008

(87) PCT Pub. No.: WO2007/099398
PCT Pub. Date: Sep. 7, 2007

(65) Prior Publication Data
US 2009/0214628 A1    Aug. 27, 2009

Related U.S. Application Data

(63) Continuation of application No. 10/596,095, filed as application No. PCT/IB2005/003665 on Sep. 27, 2005, now Pat. No. 8,916,050.

(60) Provisional application No. 60/612,919, filed on Sep. 27, 2004.

(51) Int. Cl.
| | |
|---|---|
| *A61K 8/19* | (2006.01) |
| *A61K 8/23* | (2006.01) |
| *A61K 8/25* | (2006.01) |
| *A61K 8/26* | (2006.01) |
| *A61K 8/60* | (2006.01) |
| *C02F 1/50* | (2006.01) |
| *A01N 59/06* | (2006.01) |
| *A01N 37/36* | (2006.01) |
| *A61Q 1/00* | (2006.01) |
| *A61Q 5/00* | (2006.01) |
| *A01N 59/00* | (2006.01) |
| *C02F 1/32* | (2006.01) |
| *C02F 1/78* | (2006.01) |
| *C02F 9/00* | (2006.01) |
| *C02F 103/42* | (2006.01) |

(52) U.S. Cl.
CPC ............... *C02F 1/50* (2013.01); *A01N 37/36* (2013.01); *A01N 59/00* (2013.01); *A01N 59/06* (2013.01); *A61K 8/19* (2013.01); *A61K 8/23* (2013.01); *A61K 8/25* (2013.01); *A61K 8/26* (2013.01); *A61K 8/60* (2013.01); *A61Q 1/00* (2013.01); *A61Q 5/006* (2013.01); *C02F 1/32* (2013.01); *C02F 1/78* (2013.01); *C02F 9/00* (2013.01); *C02F 2103/42* (2013.01)

(58) Field of Classification Search
CPC ............. A61K 8/18–8/29; A61K 8/60–8/608; A61Q 1/00; A61Q 5/00–5/008; A61Q 5/02; A61Q 19/00; A61Q 19/10
See application file for complete search history.

(56) References Cited

U.S. PATENT DOCUMENTS

| | | | |
|---|---|---|---|
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer et al. | |
| 2,658,072 A | 11/1953 | Kosmin | |
| 2,798,053 A | 7/1957 | Brown | |
| 2,831,854 A | 4/1958 | Tucker et al. | |
| 3,070,510 A | 12/1962 | Cooley et al. | |
| 3,155,591 A | 11/1964 | Hilfer | |
| 3,506,720 A | 4/1970 | Model et al. | |
| 3,538,230 A | 11/1970 | Pader et al. | |
| 3,553,316 A * | 1/1971 | Rubino et al. ........... | A61K 8/26 424/66 |

(Continued)

FOREIGN PATENT DOCUMENTS

| | | |
|---|---|---|
| EP | 0 251 591 | 1/1988 |
| EP | 0 273 202 | 7/1988 |

(Continued)

OTHER PUBLICATIONS

Machine translation of JP2000-063894A (2000) [online] [Retrieved Nov. 3, 2011] Retrieved from the internet <http://dossier1.ipdl.inpit.go.jp/AIPN/odse_top_dn.ipdl?N0000=7400>.*
Siegenthaler, D. (2004) "Importance of Skin's pH" [retrieved on Jun. 19, 2014] [retrieved online from http://www.naturalhealthweb.com/articles/Siegenthalerl.html].*
Definition of "Base." The MSDS Hyper Glossary. Retrieved [online] Feb. 2, 2015. Retrieved from <http://www.ilpi.com/msds/ref/base.html>.*
Definition of "compound" and "composition" from the Grant & Hackh's Chemical Dictionary (1987) p. 148, McGraw-Hill, Inc.*

(Continued)

*Primary Examiner* — Leigh C Maier
(74) *Attorney, Agent, or Firm* — Frost Brown Todd LLC

(57) ABSTRACT

The present invention relates to compositions and their use for the treatment of human skin, particularly facial skin, to alleviate the symptoms of cosmetic or determatologic skin conditions. The invention relates to compositions for treating and ameliorating skin conditions including acne, rosacea and wrinkling caused by photodamage or conditions related to aging, hormonal imbalances, hyper-pigmentation, melasma, keratosis or the like. The invention can also be used to treat conditions of the scalp such as dandruff. The present invention also relates to compositions that can be used to remove biofilms from contact lenses. More particularly, this invention relates to a composition comprising (a) one or more metasilicate; (b) one or more carbonate; (c) one or more glyconate; and (d) one or more sulfate. The composition may also contain (e) salts, e.g., sea salts and other additives or active agents.

41 Claims, No Drawings

(56) References Cited

U.S. PATENT DOCUMENTS

| | | |
|---|---|---|
| 3,862,307 A | 1/1975 | Di Giulio |
| 3,929,678 A | 12/1975 | Laughlin et al. |
| 3,956,480 A | 5/1976 | Dicter et al. |
| 3,959,458 A | 5/1976 | Agricola |
| 3,959,461 A | 5/1976 | Bailey et al. |
| 3,963,699 A | 6/1976 | Rizzie et al. |
| 3,988,433 A | 10/1976 | Benedict |
| 4,005,195 A | 1/1977 | Jandacek |
| 4,005,196 A | 1/1977 | Jandacek |
| 4,051,234 A | 9/1977 | Gieske et al. |
| 4,136,163 A | 1/1979 | Watson et al. |
| 4,138,477 A | 2/1979 | Gaffar |
| 4,152,420 A | 5/1979 | Gaffar et al. |
| 4,183,914 A | 1/1980 | Gaffar et al. |
| 4,355,028 A | 10/1982 | Kligman et al. |
| 4,387,090 A | 6/1983 | Bolich, Jr. |
| 4,443,430 A | 4/1984 | Mattei et al. |
| 4,459,425 A | 7/1984 | Amano et al. |
| 4,517,360 A | 5/1985 | Volpenhein |
| 4,518,772 A | 5/1985 | Volpenhein |
| 4,627,977 A | 12/1986 | Gaffar et al. |
| 4,725,455 A | 2/1988 | Taha |
| 4,797,300 A | 1/1989 | Jandacek et al. |
| 4,877,805 A | 10/1989 | Kligman |
| 4,892,726 A | 1/1990 | Yonekura et al. |
| 4,906,456 A | 3/1990 | Gaffar et al. |
| 4,994,262 A | 2/1991 | Charbonneau et al. |
| 5,011,681 A | 4/1991 | Ciotta et al. |
| 5,069,897 A | 12/1991 | Orr |
| 5,104,646 A | 4/1992 | Bolich, Jr. et al. |
| 5,106,609 A | 4/1992 | Bolich, Jr. et al. |
| 5,143,722 A | 9/1992 | Hollenberg et al. |
| 5,198,220 A | 3/1993 | Damani |
| 5,223,559 A | 6/1993 | Arraudeau et al. |
| 5,242,910 A | 9/1993 | Damanj |
| 5,244,664 A | 9/1993 | Godtfredsen |
| 5,294,433 A | 3/1994 | Singer et al. |
| 5,306,514 A | 4/1994 | Letton et al. |
| 5,306,515 A | 4/1994 | Letton et al. |
| 5,306,516 A | 4/1994 | Letton et al. |
| 5,454,984 A * | 10/1995 | Graubart et al. ............ 510/384 |
| 5,487,884 A | 1/1996 | Bissett et al. |
| 5,547,990 A * | 8/1996 | Hall et al. .................. 514/563 |
| 5,589,160 A | 12/1996 | Rice |
| 5,603,920 A | 2/1997 | Rice |
| 5,605,894 A * | 2/1997 | Blank et al. ................ 514/159 |
| 5,626,838 A | 5/1997 | Cavanaugh, Jr. |
| 5,651,958 A | 7/1997 | Rice |
| 5,658,553 A | 8/1997 | Rice |
| 5,688,493 A | 11/1997 | Sugawara et al. |
| 5,688,831 A | 11/1997 | El-Nokaly et al. |
| 5,733,584 A | 3/1998 | Appelt |
| 5,837,661 A | 11/1998 | Evans et al. |
| 5,883,058 A | 3/1999 | Wells et al. |
| 5,939,082 A | 8/1999 | Oblong et al. |
| 5,948,430 A | 9/1999 | Zerbe et al. |
| 6,063,397 A | 5/2000 | Fowler et al. |
| 6,177,096 B1 | 1/2001 | Zerbe et al. |
| 6,221,392 B1 | 4/2001 | Khankari et al. |
| 6,518,229 B2 * | 2/2003 | Tashjian et al. ............ 510/131 |
| 6,589,512 B1 | 7/2003 | Yue et al. |
| 6,596,298 B2 | 7/2003 | Leung et al. |
| 6,627,183 B1 | 9/2003 | Young et al. |
| 6,682,722 B2 | 1/2004 | Majeti et al. |
| 6,709,648 B2 | 3/2004 | Sako et al. |
| 6,721,987 B2 | 4/2004 | McDevitt et al. |
| 6,723,755 B2 | 4/2004 | Chomczynski |
| 2001/0043912 A1 | 11/2001 | Michael |
| 2003/0015219 A1 * | 1/2003 | Kravitz et al. ................ 134/2 |
| 2003/0026820 A1 * | 2/2003 | De Lacharriere et al. ... 424/401 |
| 2004/0101493 A1 | 5/2004 | Scott et al. |
| 2004/0101494 A1 | 5/2004 | Scott et al. |
| 2005/0003979 A1 * | 1/2005 | Lentsch et al. ............ 510/220 |
| 2005/0048025 A1 * | 3/2005 | Huang et al. ............ 424/70.31 |
| 2005/0180935 A1 * | 8/2005 | Lemoine ................ A61Q 15/00 424/66 |
| 2006/0045851 A1 | 3/2006 | Fitzgerald et al. |
| 2006/0140887 A1 | 6/2006 | Molenda et al. |
| 2007/0196311 A1 * | 8/2007 | Gross ........................ 424/70.13 |

FOREIGN PATENT DOCUMENTS

| | | | |
|---|---|---|---|
| EP | 0 441 057 | 8/1991 | |
| EP | 0 494 373 | 7/1992 | |
| EP | 0 522 624 | 1/1993 | |
| JP | 2000-63894 A * | 2/2000 | ............ C11D 7/60 |
| WO | WO 94/08557 | 4/1994 | |
| WO | WO 95/13048 | 5/1995 | |
| WO | WO 95/23780 | 9/1995 | |
| WO | WO 95/34280 | 12/1995 | |
| WO | WO 96/01101 | 1/1996 | |
| WO | WO 96/31188 | 10/1996 | |
| WO | WO 98/22085 | 5/1998 | |
| WO | WO 00/18365 | 4/2000 | |
| WO | WO 02/069753 | 9/2002 | |

OTHER PUBLICATIONS

Dadd, D.L. (2013) "Is Potassium Alum Aluminum-Free?" Retrieved from the internet [online]. Retrieved on Jun. 30, 2016. Retrieved from <http://www.debralynndadd.com/q-a/is-potassium-alum-aluminum-free/>.*

U.S. Appl. No. 09/110,409, filed Jul. 6, 1998, Shapiro et al.

U.S. Appl. No. 10/424,640, filed Apr. 25, 2003, Lawlor.

U.S. Appl. No. 10/430,617, filed May 6, 2003, Majeti et al.

Abstract—JP 70022677.

Cosmetics Science and Technology, $2^{nd}$ Ed., vol. 1, Balsam, M.S. and Sagarin, E., Editors, Krieger Publishing Co. (1992) pp. 32-43.

Drug Facts and Comparisons, Wolters Kluer Co., St. Louis, MO (1997) pp. 3-17; 54-57.

Emmert, R., "Quantification of the Soft-Focus Effect," Cosmetics & Toiletries, vol. III (Jul. 1996) pp. 57-61.

International Search Report dated Mar. 27, 2006 for Application No. PCT/IB2005/003665.

International Search Report dated Oct. 18, 2007 for Application No. PCT/IB2006/004122.

Kirk-Othmer, Encyclopedia of Chemical Technology, $4^{th}$ Ed., vol. 2, Wiley—Interscience Publishers (1992) pp. 729-737.

Niemiec et al., "Influence of Nonionic Composition on Topical Delivery of Peptide Drugs into Pilosebacious Units: A In Vivo Study using the Hamster Ear Model," Pharm. Res., vol. 12(8) (1995) pp. 1184-1188.

Patent Abstracts of Japan, vol. 2000(5) (Sep. 14, 2000) JP 2000 063894.

Preliminary Report on Patentability and Written Opinion dated Mar. 27, 2007 for Application No. PCT/IB2005/003665.

Preliminary Report on Patentability and Written Opinion dated Apr. 2, 2008 for Application No. PCT/IB2006/004122.

"Standard Practice for Particle Size Analysis of Particulate Substances in the Range of 0.2 to 75 Micrometers by Optical Microscopy," ASTM, vol. 14.02 (1993).

Office Action dated Jun. 23, 2014 for U.S. Appl. No. 10/596,095.

* cited by examiner

METHODS AND COMPOSITIONS FOR TREATMENT OF SKIN

CROSS REFERENCE TO RELATED APPLICATIONS

This application claims priority to International patent application Ser. No. PCT/IB2006/04122, filed Aug. 4, 2006, and U.S. patent application Ser. No. 10/596,095, filed May 30, 2006; the disclosures of which are hereby expressly incorporated herein by reference in their entirety for all purposes.

FIELD OF THE INVENTION

The present invention relates to compositions and methods for the treatment of human skin, particularly facial skin, to alleviate the symptoms of cosmetic or determatologic skin conditions and to improve the appearance and the feel of skin. The invention relates to compositions for treating and ameliorating skin conditions including acne, rosacea and wrinkling caused by photodamage, aging, hormonal imbalances, hyper-pigmentation, melasma, keratosis or the like. The invention also relates to a methods of treating the hair or scalp. The invention may further be used to remove biofilms from contact lenses.

BACKGROUND OF THE INVENTION

There are a variety of skin conditions—whether cosmetic or as a result of disease—that cause individuals substantial discomfort or embarrassment, making effective treatment desirable. Among these conditions are acne, rosacea, aging, skin discoloration and photodamage, psoriasis, dandruff and eczema, and dermatitis.

Acne vulgaris is an inflammatory dermatological disorder that occurs frequently in adolescence and with some regularity in older adults. The condition can include skin lesions ranging from the comedo in a pilosepaceous follicle, to more severe symptoms such as pustules, papules, cysts and nodules. The condition can be uncomfortable and embarrassing, and can result in scarring and facial disfigurement. The pathology is believed to involve a number of factors. The first is formation of comedones (more commonly referred to as whiteheads) and blackheads, made up of solid horny masses that plug follicles and are associated with increased production of sebum. As keratinized cells continue to accumulate, pressure builds up within the follicles and eventually rupture. Horny material, sebum and bacteria are dumped into the skin, provoking inflammatory responses which take the form of pustules or cystic nodules.

There are many different forms of treatment for acne vulgaris. Simple washing and cleansing is one known method. It is known in the art to use topical anti-acne agents, such as salicylic acid and benzoyl peroxide can be used to treat acne. Further, retinoids and retinols may be used, but have the undesirable side effects of mild to sever irritation, redness, peeling and itching and burning. (See U.S. Pat. No. 4,877,805 and U.S. Pat. No. 4,355,028, for example).

Another skin condition requiring treatment is rosacea. Rosacea is a common chronic skin condition characterized by a spectrum of clinical indications including flushing episodes, erythema, telangiectasia, inflammatory papulopustular eruptions resembling acne, and ocular symptoms. See U.S. Pat. No. 6,723,755, Chomczynski, et al. The etiology of rosacea is unknown, but it is presumed to be a genetically determined anomalous vascular response that develops in the third to sixth decades of life. The hypothesis that the basic pathogenesis of the disease is a flushing disorder is based on several findings. The disease appears to more prevalent in northern climates where cold exposure is experienced more often, and in light-skinned persons in whom flushing is common and sensitivity to sunlight is particularly high. Accordingly, rosacea may represent a type of hypersensitivity reaction disease in which vascular sensitivity is a central mechanism in its etiology. The correlation between sensitive blood vessels and sensitive skin has, however, not yet been determined. Epidemiological studies suggest that the regulatory mechanism of blood vessels may be of importance in the onset and development of rosacea. Studies show that 27% of rosacea patients were found to suffer from migraine and 42% from a tendency to flush, both of which represent about twice the level that would typically be found in a control group.

Psoriasis is a chronic, widespread skin disorder afflicting millions of humans and even domesticated animals. The disorder is characterized by recurrent, elevated red lesions, plaques or rarely pustules on the skin. These plaques are the results of an excessively rapid growth and shedding of epidermal (skin) cells. The cause of psoriasis is unknown.

Eczema (including but not limited to atopic, nummular and hand types) often has similar overlapping features with psoriasis. See, e.g., H. Roenigk, Jr. et al., "Psoriasis", ©1991, Marcel Dekker, Inc., Chapter 2. For instance, it is often difficult to distinguish based on clinical appearance. They can coexist, or the disease can begin as eczema and over time turn to psoriasis. Again, treatments are similar with corticosteroids and preparations commonly employed for both of these conditions.

Another skin condition commonly confined to the scalp is seborrheic dermatitis (seborrhea). The least severe form, but most common, is simple dandruff. It can become more severe and form scaly, red patches on the face, ears, chest, and other widespread areas. It often coexists with psoriasis, and many subjects have overlapping features termed "seborrhiasis." Therefore, a continuum may exist whereby these are on the same disease spectrum. Treatments are similar to those currently used for psoriasis, although lower dosages are usually sufficient to control seborrheic dermatitis.

Inflammatory skin diseases refer to diseases that are accompanied by a series of clinical signs and symptoms, such as itch, edema, erythema and abrasion are induced by various stimulative factors that cause a series of inflammatory reactions in the skin epithelium.

Seborrheic dermatitis is a dermatitis that frequently occurs on areas with a high sebum secretion, such as the scalp, the forehead and the armpit, and is also called seborrheic eczema. It causes much erythema and fine scale (dandruff) and often appears in persons in the 20-40 age group. Unlike common eczema, it is a disease resulting from abnormal constitution or sebum secretion, and is characterized in that it causes the skin to be sensitive to sunlight or heat, grows worse mainly in spring and autumn and tends to recur.

In addition to the above-described conditions, aging of the skin is a complex phenomenon that can result in skin changes that may take a variety of different forms. Skin aging can result from cigarette smoke, chemicals, ultraviolet radiation. In particular, UV radiation has led to increased prevalence of photoaging. Photoaging can be prevented by sun avoidance and proper skin protection. Skin conditions that may occur as skin ages include dry skin, zerosis, ichthyosis, brownish spots, keratoses, melasma, lentigines, age spots, liver spots, pigmented spots, wrinkles, skin lines, fine lines, oily akin, warts, eczema, pruritic skin, psoriasis, inflammatory dermatoses, or disturbed keratinization.

While there are many compounds described in the art useful for improving the appearance and condition of skin, there is still a need for compositions with improved efficacy without undesirable side effects. The present invention relates to cosmetic methods of improving skin appearance and/or condition by topical application of the subject compositions. The present invention also relates to a composition that may be used in hair color and bleaching products, shampoos, conditioners, lotions, bath oils and salts, bar soaps, facial cleansers, and foot treatments.

Toothpastes

The present invention relates to oral care compositions, including therapeutic rinses, especially mouthrinses and methods of use to provide significantly enhanced antimicrobial activity, thereby reducing oral bacteria and promoting overall oral health. Microbial populations such as *Streptococcus sanguis, Streptococcus mutans*, and *Streptococcus sobrinus* are pioneer species, the first microbial to absorb, multiply and form micro-colonies; and reduction of these species are correlated to disruption of plaque biofilm. (P. Marsh & M. Martin, Oral Microbiology, 3$^{rd}$ Edition, London, Chapman & Hall Publishers, 1996). The compositions described herein can be used to treat conditions in the oral cavity.

The present invention provides topical oral care compositions, including therapeutic rinses, especially mouth rinses, toothpastes, tooth gels, tooth powders, subgingival gels, chewing gums, mouth sprays, and lozenges (including breath mints), comprising an effective amount of the present composition for treating or preventing conditions of the oral cavity. In particular, the present invention addresses the need to remove bacteria and biofilm accumulation in the oral cavity.

Contact Lens Cleaners

The present invention also relates to compositions that can be used for the effective cleaning and disinfection of contact lenses. Deposits such as protein derived from tears or lipid derived from discharge can adhere to the surfaces of contact lenses when the lenses are worn. These deposits must be removed from the lenses prior to subsequent use. The present invention addresses the need for novel contact lens cleaners.

BRIEF SUMMARY OF THE INVENTION

The present invention relates to methods and compositions for the treatment of human skin, particularly facial skin and the scalp. The invention also relates to compositions and methods for removing biofilms in the oral cavity and from contact lenses. Where the invention is used for the treatment of skin including the scalp, the compositions are useful for imparting a visual improvement in skin appearance, for alleviating the symptoms of cosmetic or dermatologic skin conditions, or for alleviating conditions of the scalp such as dandruff.

The present invention is directed to a composition comprising (a) one or more metasilicate; (b) one or more carbonate; (c) one or more glyconate; and (d) one or more sulfate, in a topical carrier. The composition may also contain (e) salts, e.g., sea salts and/or other additives.

In a first embodiment, a composition and method for improving the appearance or condition of skin is provided wherein an effective amount of the composition described herein in a pharmaceutically or cosmetically-acceptable topical carrier is applied to the surface of the skin or to the scalp using a hair care product. The present invention is directed to a composition comprising (a) one or more metasilicate; (b) one or more carbonate; (c) one or more glyconate; and (d) one or more sulfate, in a topical carrier. The composition may also contain (e) salts, e.g., sea salts and/or other additives.

In a second embodiment, a composition and method for improving the appearance or condition of teeth or the oral cavity is provided wherein an effective amount of the composition described herein in an acceptable carrier is applied to the oral cavity. Similar to the composition described above, such the composition comprises (a) one or more metasilicate; (b) one or more carbonate; (c) one or more glyconate; and (d) one or more sulfate, in a carrier that can be delivered orally.

In a third embodiment, a composition and method for disinfecting and cleaning contact lenses is provided. The composition and method employs a composition comprising (a) one or more metasilicate; (b) one or more carbonate; (c) one or more glyconate; and (d) one or more sulfate, in a carrier that can be delivered orally.

In a further embodiment of the above-described compositions, the one or more metasilicate is an alkali metal silicate selected from the group consisting of sodium or potassium metasilicate, sodium or potassium orthosilicate and mixtures thereof.

In yet a further embodiment of the above-described compositions, the one or more carbonate is selected from the group consisting of sodium carbonate, sodium sesquicarbonate, sodium sulfate, sodium bicarbonate and mixtures thereof.

In another embodiment of the above-described compositions, the glyconate is selected from the group consisting of ammonium glyconate, lithium glyconate, sodium glyconate, sodium starch glyconate, potassium glyconate, ammonium acid glyconate, sodium acid glyconate, lithium acid glyconate, potassium acid glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

In another embodiment of the above-described compositions, the one or more sulfate is selected from the group consisting of potassium aluminum sulfate, sulfuric acid, sodium sulfate, potassium sulfate, lithium sulfate, ammonium sulfate, magnesium sulfate, strontium sulfate, aluminum sulfate, and mixtures thereof. Topical carriers include powders, lotions, gels, sprays, sticks, creams, ointments, liquids, emulsions, foams and aerosols. The compositions may also be used in combination with a fragrance, an anti-microbial such as a bactericide or fungicide, acne medications, wart remover such as salicylic acid with or without other hydroxyl acids, a reductant to bleach skin spots such as hydroxyquinone, a nutrient such as vitamin A or other vitamins and sunscreens. The composition may also be incorporated into a cosmetic, night cream, or skin ointment. Further, the composition may be used with lip balm, hand creams or lotions, bath salts or other bath additives, and treatments for hands, feet, nails, lips or the skin surrounding the eye area.

In one embodiment, the composition further comprises another cosmetically active agent What is meant by a "cosmetically active agent" is a compound that has a cosmetic or therapeutic effect on the skin, e.g., agents to treat wrinkles, acne, or to lighten the skin. In one embodiment, the agent is selected, but not limited to, from the group consisting of hydroxy acids, benzoyl peroxide, sulfur resorcinol, ascorbic acid, D-panthenol, hydroquinone, sunscreen agents, anti-inflammatory agents, skin lightening agents, antimicrobial and antifungal agents, estrogens, 2-dimethylaminoethanol, lipoic acid, amino acids such a proline and tyrosine, lactobionic acid, acetyl-coenzyme A, niacin, riboflavin, thiamin, ribose, electron transporters such as NADH and FADH2, botanical extracts such as *aloe* vera and soy, and derivatives and mixtures thereof. The cosmetically active agent will typically be present in the composition of the invention in an amount of from about 0.001% to about 20% by weight of the composition, e.g., about 0.01% to about 10%, e.g., about 0.1% to about 5%.

Examples of hydroxy acids include, but are not limited, to (i) alpha-hydroxy acids such as glycolic acid, lactic acid, malic acid, citric acid, and tartaric acid; (ii) beta-hydroxy acids such as salicylic acid; and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

DETAILED DESCRIPTION OF THE INVENTION

All percentages and ratios used herein are by weight of the total composition and all measurements made are at 25° C. unless otherwise noted. All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

One skilled in the art will readily appreciate that the present invention is well adapted to carry out the objects and obtain the ends and advantages mentioned as well as those inherent therein. It should be understood, however, that the materials, compounds, coatings, methods, procedures, and techniques described herein are presently representative of embodiments. These techniques are intended to be exemplary, are given by way of illustration only, and are not intended as limitations on the scope. Other objects, features, and advantages of the present invention will be readily apparent to one skilled in the art from the following detailed description; specific examples and claims; and various changes, substitutions, other uses and modifications that may be made to the invention disclosed herein without departing from the scope and spirit of the invention or as defined by the scope of the appended claims.

As would be known to one of ordinary skill in the art, many variations of nomenclature are commonly used to refer to a specific chemical composition. Accordingly, several common alternative names may be provided herein in quotations and parentheses/brackets, or other grammatical technique, adjacent to a chemical composition's preferred designation when referred to herein. Additionally, many chemical compositions referred to herein are further identified by a Chemical Abstracts Service registration number. As would be known to those of ordinary skill in the art, the Chemical Abstracts Service provides a unique numeric designation, denoted herein as "CAS No.," for specific chemicals and some chemical mixtures, which unambiguously identifies a chemical composition's molecular structure.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, representative embodiments of methods, devices, and materials are now described. All references, publications, patents, patent applications, and commercial materials mentioned herein are incorporated herein by reference for the purpose of describing and disclosing methodologies which are reported in the publications which might be used in connection with the invention. Nothing herein is to be construed as an admission that the invention is not entitled to antedate such disclosure by virtue of prior invention.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

DEFINITIONS

In order to provide a clear and consistent understanding of the specification and claims, including the scope to be given such terms, the following definitions are provided:

As used herein other than the claims, the terms "a," "an," "the" and "the" means one or more. As used herein in the claim(s), when used in conjunction with the words "comprises" or "comprising," the words "a," "an," "the" or "the" may mean one or more than one. As used herein "another" may mean at least a second or more.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use compositions in the real world; through inadvertent error in these procedures; through differences in the manufacture, source, or purity of the ingredients employed to make the compositions or carry out the methods; and the like. Whether or not modified by the term "about", it is intended that the claims include equivalents to the quantities.

As used herein, the term "benefit agent" includes any active ingredient that is to be delivered into and/or onto the skin, hair or nail at a desired location, such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

As used herein, the term "cosmetics" includes make-up, foundation, and skin care products. The term "make-up" refers to products that leave color on the face, including foundation, blacks and browns, i.e., mascara, concealers, eye liners, brow colors, eye shadows, blushers, lip colors, powders, solid emulsion compact, and so forth. "Skin care products" are those used to treat or care for, or somehow moisturize, improve, or clean the skin. Products contemplated by the phrase "skin care products" include, but are not limited to, adhesives, bandages, toothpaste, anhydrous occlusive moisturizers, antiperspirants, deodorants, personal cleansing products, powder laundry detergent, fabric softener towels, occlusive drug delivery patches, nail polish, powders, tissues, wipes, hair conditioners-anhydrous, shaving creams and the like. The term "foundation" refers to liquid, cream, mousse, pancake, compact, concealer or like product created or reintroduced by cosmetic companies to even out the overall coloring of the skin.

The term "dermatologically-acceptable" or "cosmetically-acceptable" as used herein, means that the compounds or composition(s) which the term describes are suitable for use in contact with tissues (e.g., the skin) without undue toxicity, incompatibility, instability, irritation, allergic response and the like. This term is not intended to limit the compound/composition to which it describes for use solely as a cosmetic (i.e., the ingredient/product may be used as a pharmaceutical).

As used herein, "relief of symptoms" refers to decrease in severity over that expected in the absence of treatment and does not necessarily indicate a total elimination or cure of the disease. Relief of symptoms is also intended to include prophylaxis.

As used herein, "topically applying" means directly laying on or spreading on outer skin, e.g., by use of hands or an applicator such as a wipe, puff, roller or spray.

As used herein, the term "safe and effective amount" means an amount of compound(s) or composition(s) sufficient to treat acne or other skin conditions described herein, but low enough to avoid serious side effects, i.e., to provide a reasonable benefit-to-risk ratio, within the scope of sound medical judgment.

As used herein, the term "treating" or "treatment" means the treatment (e.g., alleviation or elimination of symptoms and/or cure) and/or prevention or inhibition of the condition (e.g. a skin condition) or relief of symptoms.

Compositions

The present invention relates to compositions and their use for the treatment skin, particularly facial skin, or the scalp. The present invention is directed to a conditioning composition comprising (a) one or more metasilicate; (b) one or more carbonate; (c) one or more glyconate; and (d) one or more sulfate. The composition may also contain (e) salts, e.g., sea salts, and other additives. The composition may also include other active ingredients.

The present invention also relates to compositions and their use for the treatment of the oral cavity.

The present invention also relates to compositions and their use for the treatment of contact lenses.

The present invention is directed to compositions comprising:
(a) one or more metasilicates
(b) one or more carbonate;
(c) one or more glyconate; and
(d) one or more sulfate or aluminum salt.

In one embodiment, the composition further comprises (e) an inorganic salt.

In another specific embodiment, the present invention provides for a composition additionally comprising:
(e) one or more inorganic salt.

In another specific embodiment, the present invention provides for a composition additionally comprising:
(f) one or more additional ingredients.

In another specific embodiment, the present invention provides for a composition additionally comprising:
(f) one or more additional active ingredients.

Metasilicate

The present invention may include one or more metasilicate which may be an alkali metal silicate selected from the group consisting of sodium or potassium metasilicate, sodium or potassium orthosilicate and mixtures thereof. In one embodiment, the metasilicate is incorporated in the final composition in an amount of 0.01%-5.0%, or 0.1-4.0%, based on the total amount of the composition.

Carbonate

In another embodiment, the carbonate used in the present invention is one or more carbonates selected from the group consisting of sodium carbonate, potassium carbonate, sodium bicarbonate, potassium bicarbonate, and sodium sesquicarbonate. In another embodiment, the carbonate used in the present invention is sodium carbonate and sodium bicarbonate. In another embodiment, the carbonates is incorporated in the final composition in an amount of 0.01%-4.0%, or 0.1-3.0%, based on the total amount of the composition.

Typical carbonates include sodium carbonate ($Na_2CO_3$), potassium carbonate ($K_2CO_3$) or other typical carbonate sources. Such carbonates can contain as an impurity some proportion of bicarbonate ($HCO_3^-$).

In one embodiment, the composition further comprises peroxygen compound. The peroxygen compound is preferably a perborate or a percarbonate and more preferably a percarbonate. The perborate or percarbonate preferably is complexed with a metal such as sodium, lithium, calcium, potassium or boron. The percent by weight of the peroxygen compound in the final composition ranges from about 0.01%-4.0%, or 0.1-3.0%, based on the total amount of the composition.

In another embodiment, the carbonate is a builder wherein the builder is at least one of the following compounds: a sodium carbonate (e.g., soda ash), sodium sesquicarbonate, sodium sulfate or sodium bicarbonate. A builder is also known as a sequestrant. A "sequestrant" is a molecule capable of coordinating (i.e., binding) metal ions to prevent the metal ions from interfering with the action of the other ingredients of the composition. Some chelating/sequestering agents can also function as a threshold agent when included in an effective amount. Optionally, the builders can be added, e.g., water soluble inorganic salt builders, preferably sodium salts, such as sodium polyphosphates, e.g. sodium tripolyphosphate and sodium pyrophosphate, sodium carbonate, sodium bicarbonate, sodium sesquicarbonate, sodium silicate, sodium disilicate, sodium metasilicate and sodium borate. In addition to the water soluble inorganic salts, water insoluble builders may also be useful, including the ion exchanging zeolites, such as Zeolite 4A. Organic builders may also be employed. Among suitable organic builders are polyacetal carboxylates, as described in U.S. Pat. No. 4,725,455, and water-soluble salts of lower hydroxycarboxylic acids, such as an alkali metal gluconate.

In one embodiment, the carbonate is a hydrated carbonate such as trona. In one embodiment, the percent by weight of the builder is from about 0.01%-4.0%, or 0.1-3.0%, based on the total amount of the composition. In another embodiment, the peroxygen compound, metasilicate and chelate are all salts having the same cation. In one embodiment, the cation is sodium or potassium.

Glyconate

In one embodiment, the glyconate is selected from the group consisting of ammonium glyconate, lithium glyconate, sodium glyconate, sodium starch glyconate, potassium glyconate, ammonium acid glyconate, sodium acid glyconate, lithium acid glyconate, potassium acid glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

In one embodiment, the percent by weight of the builder is from about 0.001%-0.4%, or 0.01-0.3%, based on the total amount of the composition.

Sulfate or Aluminum Salts

Examples of aluminum salts suitable for use in the present invention include inorganic aluminum salts such as potassium aluminum sulfate, ammonium aluminum sulfate and aluminum chloride; and soluble aluminum carboxylates such as aluminum lactate, aluminum citrate and aluminum maleate.

Regarding these aluminum salts, in one embodiment, at least 90% by weight (hereinafter referred to as "%") or more of their particles have diameters of 200 micrometers or less. In one embodiment, at least 90% or more of the particles which make up the composition have diameters of 200 micrometers or less, and, in one embodiment, the average particle diameter falls within a range of 20-150. Ideally, the average particle diameter should be between 20 and 100 micrometers. These aluminum salts can be used singly or in combination.

Salts

In one embodiment, the composition contains a salt. The salt should not interfere with the biological activity of the composition. When other materials are present, the salt should not degrade those materials or interfere with their properties or biological activity. In other words, the salt should be inert with respect to the other components.

The salt may be a single salt material or a mixture of two or more salts alone. When the carrier matrix contains a mixture of salts, those salts are preferably present in equal amounts, e.g., a mixture of two salts in a 1:1 ratio.

Examples of suitable salts include various alkali metal and/or alkaline earth metal sulfates, chlorides, borates, bromides, citrates, acetates, lactates, etc. Specific examples of suitable salts include, but are not limited to, sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate and lithium chloride. The preferred salts are the inorganic salts, such as the Group 1 or 2 metal sulfates and chlorides. Particularly preferred salts, because of their low cost, are sodium sulfate, and sodium chloride. Sodium chloride may be substantially pure or in the form of rock salt, sea salt, or dendrite salt.

In another embodiment, the composition, prior to final use, is prepared as a composition comprising:

| Meta Silicate | about 0.7-3.3% wt |
| Carbonate | about 0.7-1.7% wt |

-continued

| Glyconate | about 0.33-1.7% wt |
| Aluminum Sulfate | about 0.33-1.7% wt |

In another embodiment, the composition, prior to final use, is prepared as a composition comprising:

| Meta Silicate | about 1.33-2.0% wt |
| Carbonate | about 1.33-1.7% wt |
| Glyconate | about 0.33-0.7% wt |
| Potassium Al Sulfate | about 0.33-0.7% wt |

In another embodiment, the composition, prior to final use, is prepared as a composition comprising:

| MetaSilicate | about 0.7-3.3% wt |
| Carbonate | about 0.7-3.3% wt |
| Glyconate | about 0.33-1.7% wt |
| Potassium Al Sulfate | about 0.33-1.7% wt |
| Inorganic Salt | about 0.33-1.7% wt |

In another embodiment, the composition, prior to final use, is prepared as a composition comprising:

| Meta Silicate | about 1.3-2.0% wt |
| Carbonate | about 1.3-1.7% wt |
| Glyconate | about 0.3-0.7% wt |
| Potassium Al Sulfate | about 0.3-0.7% wt |
| Inorganic Salt | about 0.3-0.7% wt |

In another embodiment, the composition, prior to final use, is prepared as a composition comprising:

| Meta Silicate | about 1.63% wt |
| Sodium Carbonate | about 1.5% wt |
| Sodium Glyconate | about 0.5% wt |
| Potassium Al Sulfate | about 0.5% wt |

In another embodiment, the composition, is prepared as a composition comprising:

| Meta Silicate | about 1.63% wt |
| Sodium Carbonate | about 1.5% wt |
| Sodium Glyconate | about 0.5% wt |
| Inorganic salt | about 0.5% wt |
| Potassium Al Sulfate | about 0.5% wt |

In one specific embodiment, the present invention provides for a composition comprising:
(a) at least 0.0001% wt of one or more metasilicates;
(b) at least 0.0001% wt of one or more carbonate
(c) at least 0.00005% wt of one or more glyconate; and
(d) at least 0.00002% wt of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in final composition.

In another specific embodiment, the present invention provides for a composition additionally comprising:
(e) at least 0.00006% wt of one or more salts.

In one specific embodiment, the present invention provides for a composition comprising:
(a) at least 0.0001% wt of one or more metasilicates;
(b) at least 0.0002% wt of one or more carbonate
(c) at least 0.00008% wt of one or more glyconate; and
(d) at least 0.00008% wt of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in the final composition.

In another specific embodiment, the present invention provides for a composition additionally comprising:
(e) at least 0.0001% wt of one or more salts.

In one specific embodiment, the present invention provides for a composition comprising:
(a) at least 0.0003% wt of one or more alkali metal silicate selected from the group consisting of sodium or potassium metasilicate, orthosilicate or other water-soluble silicate;
(b) at least 0.0003% wt of one or more carbonate selected from the group consisting of sodium carbonate, sodium sesquicarbonate, sodium sulfate and sodium bicarbonate;
(c) at least 0.00009% wt of one or more glyconate; and
(d) at least 0.00008% wt of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in final composition.

In another specific embodiment, the present invention provides for a composition additionally comprising:
(e) at least 0.00006% wt of one or more salts.

In one specific embodiment, the present invention provides for a composition comprising:
(a) at least 0.00011% wt of metasilicates;
(b) at least 0.0002% wt of sodium carbonate
(c) at least 0.00008% wt of sodium glyconate; and
(d) at least 0.00008% wt of potassium aluminum sulfate;
wherein the concentrations are the concentration in the final composition.

In another specific embodiment, the present invention provides for a composition additionally comprising:
(e) at least 0.0001% wt of one or more salts.

In one specific embodiment, the present invention provides for a composition comprising:
(a) from about 0.0001 to about 0.0100% wt of one or more metasilicates;
(b) from about 0.0001 to about 0.0100% wt of one or more
(c) from about 0.00001 to about 0.0060% wt of one or more glyconate; and
(d) from about 0.00001 to about 0.0100% wt one or more sulfate,
wherein the concentrations are the concentration in final composition.

In another specific embodiment, the present invention provides for a composition additionally comprising:
(e) from about 0.0001 to about 0.0100% wt of one or more salts.

In one specific embodiment, the present invention provides for a composition comprising:
(a) from about 0.0001 to about 0.0010% wt of one or more metasilicates;
(b) from about 0.0001 to about 0.0010% wt of one or more carbonate
(c) from about 0.000001 to about 0.0006% wt of one or more glyconate; and
(d) from about 0.0001 to about 0.0010% wt of potassium aluminum sulfate,
wherein the concentrations are the concentration in final composition.

In another specific embodiment, the present invention provides for a composition additionally comprising:
(e) from about 0.0001 to about 0.0010% wt of one or more salts.

The substances to be used in the compositions of the present invention are generally utilized within the following ranges:

TABLE 1

| Substance | % Weight of Total Composition |
| --- | --- |
| Meta Silicate | 0.01-10.0 |
| Sodium Carbonate | 0.01-8.50 |
| Sodium Glyconate | 0.00001-5.40 |
| Sea salt | 0.01-9.20 |
| Potassium Al Sulfate | 0.00015-0.0830 |
| Meta Silicate | 0.011-5.0 |
| Sodium Carbonate | 0.017-7.20 |
| Sodium Glyconate | 0.005-4.20 |
| Sea salt | 0.006-3.00 |
| Potassium Al Sulfate | 0.009-2.75 |
| Meta Silicate | 0.012-0.07 |
| Sodium Carbonate | 0.029-0.048 |
| Sodium Glyconate | 0.008-0.035 |
| Sea salt | 0.006-0.028 |
| Potassium Al Sulfate | 0.002-0.0190 |
| Meta Silicate | 0.035-0.065 |
| Sodium Carbonate | 0.032-0.04 |
| Sodium Glyconate | 0.009-0.014 |
| Sea salt | 0.01-0.0135 |
| Potassium Al Sulfate | 0.008-0.0135 |
| Fragrances | 0.01-0.011 |

TABLE 2

| Ranges Specific to Particular Embodiments | |
| --- | --- |
| Composition | % Weight of Total Composition |
| Cosmetics/Skin Care Products | |
| Meta Silicate | 0.21-0.42 |
| Sodium Carbonate | 0.16-0.32 |
| Sodium Glyconate | 0.06-0.13 |
| Potassium Al Sulfate | 0.06-0.13 |
| Meta Silicate | 1-5 |
| Sodium Carbonate | 0.5-5 |
| Sodium Glyconate | 0.1-2 |
| Potassium Al Sulfate | 0.1-2 |
| Meta Silicate | 2-10 |
| Sodium Carbonate | 1-10 |
| Sodium Glyconate | 0.5-5 |
| Potassium Al Sulfate | 0.5-5 |
| Shampoos/Hair Care Product | |
| Meta Silicate | 0.04-1.6 |
| Sodium Carbonate | 0.03-1.2 |
| Sodium Glyconate | 0.01-0.04 |
| Potassium Al Sulfate | 0.01-0.04 |
| Meta Silicate | 0.2-5 |
| Sodium Carbonate | 0.1-5 |
| Sodium Glyconate | 0.1-2 |
| Potassium Al Sulfate | 0.1-2 |
| Meta Silicate | 0.2-10 |
| Sodium Carbonate | 0.1-10 |
| Sodium Glyconate | 0.1-5 |
| Potassium Al Sulfate | 0.1-5 |

TABLE 2-continued

Ranges Specific to Particular Embodiments

| Composition | % Weight of Total Composition |
|---|---|
| Toothpaste/Oral Care Products | |
| Meta Silicate | 0.08-3.2 |
| Sodium Carbonate | 0.6-2.4 |
| Sodium Glyconate | 0.02-0.08 |
| Potassium Al Sulfate | 0.02-0.08 |
| Meta Silicate | 0.2-10 |
| Sodium Carbonate | 1-10 |
| Sodium Glyconate | 0.2-4 |
| Potassium Al Sulfate | 0.2-4 |
| Meta Silicate | 1-20 |
| Sodium Carbonate | 1-20 |
| Sodium Glyconate | 0.5-10 |
| Potassium Al Sulfate | 0.5-10 |
| Contact Lens Cleaner | |
| Meta Silicate | 0.16-6.4 |
| Sodium Carbonate | 1.2-4.8 |
| Sodium Glyconate | 0.04-0.16 |
| Potassium Al Sulfate | 0.04-0.16 |
| Meta Silicate | 0.2-10 |
| Sodium Carbonate | 1-10 |
| Sodium Glyconate | 0.2-4 |
| Potassium Al Sulfate | 0.2-4 |
| Meta Silicate | 1-20 |
| Sodium Carbonate | 1-20 |
| Sodium Glyconate | 0.5-10 |
| Potassium Al Sulfate | 0.5-10 |

Uses of the Present Invention Related to Skincare

The topical formulations of the invention contain the metasilicate, carbonate, glyconate, and sulfate ingredients in a concentration effective to prevent or reduce (hereafter, "inhibit") the skin irritation (such as itching, dry skin, inflammation) symptoms that are sought to be eliminated. In one embodiment, the formulation contains the ingredients in a suitable topical vehicle at a total concentration of about 10 to about 5000 mM. In another embodiment, the formulation contains the ingredients in a suitable topical vehicle at a total concentration of about 25 to about 3000 mM. In another embodiment, the formulation contains the ingredients in a suitable topical vehicle at a total concentration of about 50 to about 2000 mM. In another embodiment, the formulation contains the ingredients in a suitable topical vehicle at a total concentration of about 100 to about 1000 mM. In another embodiment, the formulation contains the ingredients in a suitable topical vehicle at a total concentration of about 200 to about 500 mM. In another embodiment, the formulation of the invention includes additional ingredients such as an exfoliant ingredient.

The compositions and methods of the present invention are useful for treating follicular diseases such as acne, rosacea, hyperlipidemia, seborrhea, sebaceous hyperplasia, follicular rash, demodex folliculorum follicular infections such as folliculitis, staphylococcal impetigoacne necrotica, and pseudofollicuitis barbe, follicular keratosis, keratosis pilaris, phrynoderma, ichthyosis follicularis, alopecia, follicular dysplasia, hirsutism, oily skin and hypertrichosis. In one embodiment, the present invention relates to topical compositions that may also include an anti-acne agent. Examples of anti-acne agents include, but are not limited to, salicylic acid, benzoyl peroxide, sulphur, retinoic acid, *candida bombicola*/glucose/methyl rapeseedate ferment, peat water, resorcinol, silt, peat, permethin, azelaic acid, clindamycin, adapalene, erythromycin, sodium sulfacetamide, and combinations thereof. In one embodiment, the amount of anti-acne agent in the composition is from about 0.01% to about 10%, for example from about 0.1% to about 5% or from about 0.5% to about 2% by weight, based on the total weight of the composition.

The compositions and methods of the present invention are also useful for evening skin tone (such as lightening dark areas of skin) in need of such treatment, smoothing the skin (such as reducing texture on the skin), reducing the production of sebum, and reducing the appearance of oil, shine, and/or pores on skin in need of such treatment. Examples of skin in need of such treatment include, but are not limited to, skin having excessive pigmentation (such as freckles, post-inflammatory hyperpigmentation (PIH), or pigmented scars), rough skin, oily skin or skin having large, visible pores. In another embodiment, the present invention relates to topical compositions that may also include other active ingredients known to improve skin condition or appearance.

The compositions and methods of the present invention are also useful for the treatment of skin conditions such as eczema. In one embodiment, the present invention relates to topical compositions that may also include other active ingredients known to improve or treat eczema. In other embodiments, the present invention may be used for the treatment of rosacea. In yet another embodiment, the present invention may also include one or more anti-rosacea agents.

In one embodiment, the composition is heated prior to application. In one embodiment, the temperature of the composition should not exceed a temperature of 100° F.

In one embodiment, the present invention is directed to a cosmetic composition and corresponding methods of applying the composition directly to the skin or scalp, wherein the composition comprises from about 0.1% to about 50% by weight of the conditioning composition and from about 50% to about 99.9% by weight of a suitable carrier.

In one embodiment, the present invention is directed to a cosmetic composition and corresponding methods of applying the composition directly to the skin or scalp, wherein the composition comprises from about 0.1% to about 40% by weight of the conditioning composition, from about 0.005% to about 20% by weight of a salt, and from about 40% to about 99% by weight of a suitable carrier.

In one embodiment, the present invention is directed to a cosmetic composition and corresponding methods of applying the composition directly to the skin or scalp, wherein the composition comprises from about 0.1% to about 20% by weight of the conditioning composition, from about 0.005% to about 20% by weight of a benefit agent, and from about 60% to about 99% by weight of a suitable carrier.

In another embodiment, the composition is a leave-on cosmetic composition and corresponding methods of applying the composition directly to the scalp, wherein the composition comprises from about 0.1% to about 20% by weight of the conditioning composition, from about 0.005% to about 20% by weight of a moisturizing agent or carrier, and from about 40% to about 99% by weight of a volatile liquid.

In another embodiment, the composition further comprises a thickening polymer in an amount of 0.01 to 20 wt % based on the weight of the conditioning composition.

In another embodiment, the composition further comprises one or more of at least one amphoteric surfactant; at least one nonionic surfactant or at least one phospholipid; and at least one wax; wherein the ingredients are present in a combined amount sufficient to allow the conditioning composition to be incorporated into an aqueous solution In another embodiment, the composition further comprises a fatty alcohol present in an amount of from about 2.5% to about 4% by weight of the composition.

In another embodiment, the composition further comprises water present in an amount of from about 60% to about 96% by weight of the composition.

In another embodiment, the composition further comprises at least one of the following additives: a thickener, a dye, a fragrance, and/or a preservative.

Benefit Agents

The compositions of the present invention may be used as a skin conditioning system. The skin conditioning system may further contain one or more benefit agents or pharmaceutically-acceptable salts thereof. The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the conditioning system.

Examples of suitable benefit agents include, but are not limited to, depigmentation agents; reflectants; detangling/wet combing agents; film forming polymers; humectants; amino acids and their derivatives; antimicrobial agents; allergy inhibitors; anti-acne agents; anti-aging agents; anti-wrinkling agents antiseptics; analgesics; antitussives; antipruritics; local anesthetics; anti-hair loss agents; hair growth promoting agents; hair growth inhibitor agents, antihistamines such as *Mandragora Vernalis, Tanacetum Parthenium* and the like; antiinfectives such as *Acacia Catechu, Aloe Barbadensis, Convallaria Majalis, Echinacea, Eucalyptus, Mentha Piperita, Rosa Canina, Sassafras Albidum*, and the like; inflammation inhibitors; anti-emetics; anticholinergics; vasoconstrictors; vasodilators; wound healing promoters; peptides, polypeptides and proteins; deodorants and antiperspirants; medicament agents; skin emollients and skin moisturizers; skin firming agents, hair conditioners; hair softeners; hair moisturizers; vitamins; tanning agents; skin lightening agents; antifungals such as Centaurea Cyanus, Kalmia Latifolia and antifungals for foot preparations; depilating agents; shaving preparations, external analgesics; perfumes; counterirritants; hemorrhoidals; insecticides, poison ivy products; poison oak products; burn products; anti-diaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens, those active ingredients disclosed in U.S. Pat. No. 6,063,397, which is incorporated herein by reference, anti-edema agents, collagen enhancers, and mixtures thereof.

Examples of suitable anti-edema agents nonexclusively include bisabolol natural, synthetic bisabolol, and mixtures thereof.

Examples of suitable vasoconstrictors nonexclusively include horse chestnut extract, prickly ash, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene, oat oil, chamomile, and mixtures thereof.

Examples of collagen enhancers nonexclusively include vitamin A, vitamin C, and mixtures thereof.

Examples of suitable skin firming agent nonexclusively include dimethylaminoethanol ("DMAE").

Examples of suitable antipruritics and skin protectants nonexclusively include oatmeal, betaglucan, feverfew, soy and derivatives thereof, bicarbonate of soda, colloidal oatmeal, surfactant based colloidal oatmeal cleanser, *Anagallis Arvensis, Oenothera Biennis, Verbena Officinalis*, and the like. These antipruritics may be used in an amount, based upon the total weight of the skin conditioning composition, from about 0.01 percent to about 40 percent, and preferably from about 1 percent to about 5 percent.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size.

Examples of suitable reflectants nonexclusively include mica, alumina, calcium silicate, glycol dioleate, glycol distearate, silica, sodium magnesium fluorosilicate, and mixtures thereof.

Suitable detangling/wet combing agents nonexclusively include polyquaternium-10, hydroxypropyltrimonium guar, dioleoylamidoethyl hydroxyethylmonium methosulfate, di-(soyoylethyl)hydroxyethylmonium methosulfate, hydroxyethyl behenamidopropyl dimonium chloride, olealkonium chloride, polyquaternium-47, stearalkonium chloride, tricetylmonium chloride, and mixtures thereof.

Suitable film forming polymers include those that, upon drying, produce a substantially continuous coating or film on the heir, skin, or nails. Nonexclusive examples of suitable film forming polymers include acrylamidopropyl trimonium chloride/acrylamide copolymer; corn starch/acrylamide/sodium acrylate copolymer, polyquaternium-10; polyquaternium-47; polyvinylmethylether/maleic anhydride copolymer; styrene/acrylates copolymers; and mixtures thereof.

Commercially available humectants which are capable of providing moisturization and conditioning properties to the skin conditioning composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula I.: HO—(R"O)$_b$—H I. wherein R" is an alkylene group having from about 2 to about 4 carbon atoms and b is an integer of from about 1 to about 10, such as PEG 4; 3) polyethylene glycol ether of methyl glucose of formula II.: CH$_3$—C$_6$H$_{10}$O$_5$—(OCH$_2$CH$_2$)$_c$—OH II. wherein c is an integer from about 5 to about 25; 4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, caproyl silk amino acid, caproyl collagen amino acids; caproyl keratin amino acids; caproyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

In one embodiment, the composition further comprises a nutrient. What is meant by a nutrient is an organic substance occurring in foods that is not synthesized by the body and is necessary in trace amounts for the normal metabolic functioning of the body, such as vitamins, essential amino acids, and essential fatty acids.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A, C, D, E, K and their derivatives such as vitamin A palmitate and pro-vitamins, e.g. (i.e. panthenol (pro vitamin B5) and panthenol triacetate) and mixtures thereof.

Examples of such essential amino acids include, but are not limited to, arginine, histidine, isoleucine, leucine, lysine, methionine, phenylalanine, threonine, tryptophan, and valine. Examples of essential fatty acids include, but are not limited to, linoleate and linolenate.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

Examples of suitable hair conditioners nonexclusively include quaternized compounds such as behenamidopropyl PG-dimonium chloride, tricetylmonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula III. ##STR00001## wherein $R_5$ is a branched or unbranched alkyl group having about 1 to about 6 carbon atoms; $R_6$ is H, methyl or ethyl; $R_7$ is a branched or unbranched alkyl or alkoxy group having from about 1 to about 8 carbon atoms; and K is a —CN or a —COOR$_6$ group, wherein $R_6$ is a branched or unbranched alkyl group having from about 1 to about 6 carbon atoms, natural or synthetic pyrethroids, whereby the natural pyrethroids are contained in pyrethrum, the extract of the ground flowers of *Chrysanthemum cinerariaefolium* or *C. coccineum*; and mixtures thereof. Within the structure of Formula III are ethyl 3-(N-butylacetamido)propionate, wherein $R_7$ is a $CH_3$ group, $R_5$ is an n-butyl group, $R_6$ is H, K is COOR$_8$ and $R_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, *capsicum, capsicum* oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, *Fragaria Vesca, Matricaria Chamomilla*, and *Salvia Officinalis*.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Most preferred benefit agents nonexclusively include DMAE, soy and derivatives thereof, colloidal oatmeal, sulfonated shale oil, olive leaf, elubiol, 6-(1-piperidinyl)2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erythromycin, tretinoin, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the skin conditioning composition or the emulsion may vary depending upon, for example, the ability of the benefit agent to penetrate through the skin, hair or nail, the specific benefit agent chosen, the particular benefit desired, the sensitivity of the user to the benefit agent, the health condition, age, and skin, hair, and/or nail condition of the user, and the like. In sum, the benefit agent is used in a "safe and effective amount," which is an amount that is high enough to deliver a desired skin, hair or nail benefit or to modify a certain condition to be treated, but is low enough to avoid serious side effects, at a reasonable risk to benefit ratio within the scope of sound medical judgment. Unless otherwise expressed herein, typically the benefit agent is present in the skin conditioning system in an amount, based upon the total weight of the system, from about 0.01 percent to about 20.0 percent, and preferably from about 0.01 percent to about 5.0 percent, and more preferably from about 0.01 percent to about 2.0 percent.

Optionally, commercially available detergent thickeners that are capable of imparting the appropriate viscosity to conditioning shampoo compositions are suitable for use in this invention. If used, the detergent thickeners should be present in the shampoo compositions in an amount sufficient to raise the Brookfield viscosity of the composition to a value of between about 500 to about 10,000 centipoise. Examples of suitable detergent thickeners nonexclusively include: mono or diesters of polyethylene glycol of formula IV. HO—(CH$_2$CH$_2$O)$_z$H IV. wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable detergent thickeners nonexclusively include behenalkonium chloride; cetyl alcohol, quaternium-46, hydroxyethyl cellulose, cocodimonium chloride, polyquaternium-6, polyquaternium-7, quaternium-18, PEG-18 glycerol oleate/cocoate, a mixture of acrylates/steareth-50 acrylate copolymer, laureth-3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Anti 414 liquid," and mixtures thereof. Preferred detergent thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

In another embodiment, the compositions of the present invention are useful as a cleansing system and cleansing composition In one embodiment, the cleansing system and cleansing composition may also optionally contain a foaming surfactant. The foaming surfactant may be non-ionic, cationic, amphoteric, or anionic; nonionic surfactants are preferred. By "foaming," it is meant that the surfactant, when used with the composition of the present invention, has a column height of foam greater than about 20 mm as determined by the Ross-Miles Test. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition.

The above described skin conditioning composition and cleaning system may be prepared by combining the desired components in a suitable container and mixing them under ambient conditions in any conventional mixing means well known in the art, such as a mechanically stirred propeller, paddle, and the like.

Another embodiment of the present invention is directed to a method for depositing a benefit agent onto the skin, hair and/or nails comprised of applying either the above-described skin conditioning system or cleansing composition with an effective amount of a benefit agent to a desired location on a human or animal. While the frequency and amount of the benefit agent-containing cleaning system to be applied will depend upon, for example, the type and amount of benefit agent available, the intended usage of the final composition, i.e. therapeutic versus maintenance regimen, the amount and type of detergent present, and the sensitivity of the individual user to the composition/emulsion, typically the benefit agent-containing cleaning system of the present invention should be topically applied to affected body parts at regular intervals, and preferably from about 2 to about 14 times per week. More preferably, the composition/emulsion is applied more frequently during the initial stages of treatment, e.g. from about 5 to about 7 times per week until the desired effect is achieved, then less frequently when maintenance is desired, e.g. from about 2 to about 5 times per week.

The above-described skin conditioning composition and cleansing system are capable of efficiently mediating the deposition and permeation of various benefit agents, such as antidandruff agents, onto and into the skin following topical administration thereto.

An alternative preferred embodiment of the present invention is directed to a method for treating hair loss, such as hair loss resulting from alopecia, comprising topically applying the above-described cleaning system and the hair loss benefit agent to a desired location on an animal or human, wherein the benefit agent is comprised of an effective amount of a hair loss treatment agent such as minoxidil or mixture thereof. As used herein, "hair loss treatment agents" shall include agents capable of growing hair and/or agents capable of preventing the loss of hair. By "effective amount," it is meant an amount effective for treating hair loss and preferably may range from, based upon the total weight of the skin conditioning system, from about 0.001 percent to about 20 percent, and preferably from about 1 percent to about 5 percent.

Examples of benefit agents suitable for treating hair loss include, but are not limited to potassium channel openers or peripheral vasodilators such as minoxidil, diazoxide, and compounds such as N*-cyano-N-(tert-pentyl)-N'-3pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin E1 and prostaglandin F2-alpha; fatty acids, such as oleic acid; diuretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucocorticoids such as betamethasone; botanical extracts such as *aloe*, clove, ginseng, *rehmannia, swertia*, sweet orange, *zanthoxylum, Serenoa repens* (saw palmetto), *Hypoxis rooperi*, stinging nettle, pumpkin seeds, and rye pollen; other botanical extracts including sandlewood, red beet root, *chrysanthemum*, rosemary, burdock root and other hair growth promoter activators which are disclosed in DE 4330597 which is incorporated by reference in its entirety herein; homeopathic agents such as Kalium Phosphoricum D2, *Azadirachta indica* D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothiazines; pinacidil; psoralens, verapamil; zidovudine; alpha-glycosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof.

Preferred hair loss treatment agents include minoxidil, 6-(1-piperidinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

Another embodiment of the present invention is directed to a method for inhibiting hair growth comprising topically applying the above-described composition/system combined with a benefit agent to a desired area on an animal or human for inhibiting hair growth, wherein the benefit agent is comprised of an effective amount of a hair growth inhibiting agent. In a preferred embodiment, the cleaning system contains, based upon the total weight of the cleaning system, from about 0.001 percent to about 20 percent, and preferably from about 0.01 percent to about 5 percent hair growth inhibiting agent.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethasone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; intraconazole; levodopa; maprotiline; methysergide; metoprolol; metyrapone; nadolol; nicotinic acid; potassium thiocyanate; propranolol; pyridostigmine; salicylates; sulfasalazine; terfenadine; thiamphenicol; thiouracils; trimethadione; troparanol; valproic acid; and mixtures thereof.

Preferred hair growth inhibitory agents include serene proteases, retinol, isotretinoin, betamethasone, alpha-tocophenol and derivatives thereof, or mixtures thereof.

Another preferred embodiment of the present invention is directed to a method for treating acne and for reducing the signs of aging, i.e. wrinkles, fine lines, and other manifestations of photodamage, comprising topically applying the above-described cleaning system and the relevant benefit agent to the skin of an animal or human at a desired area, wherein the benefit agent is comprised of an effective amount of an anti-acne agent or an anti-aging agent, respectively.

Examples of suitable anti-aging agents include, but are not limited to inorganic sunscreens such as titanium dioxide and zinc oxide; organic sunscreens such as octyl-methoxy cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaprolc acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, *aloe*, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, anti-oxidants, alpha-hydroxy acids and beta-hydroxy acid with retinol and tretinoin being most preferred. Suitable amounts of anti-aging agents include, based upon the total weight of the described cleaning system, from about 0.01 percent to about 20 percent, and preferably from about 0.04 percent to about 5 percent.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as *alnus, arnica, artemisia capillaris, asiasarum* root, birrh, *calendula*, chamomile, *cnidium*, comfrey, fennel, galla rhois, hawthorn, *houttuynia, hypericum*, jujube, kiwi, licorice, magnolia, olive, peppermint, philodendron, *salvia, sasa albo-marginata*; imidazoles such as ketoconazole and elubiol, and those described in Gollnick, H et al. 196(I) Dermatology Sebaceous Glands, Acne and Related Disorders, 119-157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Suitable amount of anti-acne agents include, based upon the total weight of the described cleaning system, from about 0.01 percent to about 10 percent, and preferably from about 0.04 percent to about 5 percent.

Another preferred embodiment of the present invention is directed to a method for depigmenting the skin, comprising topically applying to skin at a desired area the above-described cleaning system and an effective amount of the depigmentation benefit agent. Suitable effective amounts of depigmentation agents include, based upon the total weight of the described cleaning system, from about 0.01 percent to about 10 percent, and preferably from about 0.04 percent to about 5 percent.

Examples of suitable depigmentation agents include, but are not limited to soy and derivatives thereof, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinol, Kojic acid, and hydroquinone, being preferred.

An alternative preferred embodiment of the present invention is directed to a method for treating the symptoms and/or the diseases of dandruff, seborrheic dermatitis and/or psoriasis, comprising topically applying the above-described cleaning system and the relevant benefit agent to a location desired wherein the benefit agent is comprised of an effective amount of a dandruff treatment agent, a seborrheic dermatitis treatment agent, or a psoriasis treatment agent, respectively. As used herein, "dandruff treatment agent," "seborrheic dermatitis treatment agent," or a "psoriasis treatment agent," respectively, shall include agents capable of treating the symptoms and/or the diseases of dandruff, seborrheic dermatitis, and psoriasis, respectively. By "effective amount," it is meant an amount effective for treating the disease and/or the symptoms associated therewith and preferably may range from, based upon the total weight of the cleaning system, from about 0.001 percent to about 10 percent, and preferably from about 0.01 percent to about 5 percent.

Examples of benefit agents suitable for treating the symptoms and/or the diseases of dandruff, seborrheic dermatitis and/or psoriasis, respectively, nonexclusively include those set forth above with shale oil and derivatives thereof, elubiol, ketoconazole, coal tar, salicylic acid, zinc pyrithione, selenium sulfide, hydrocortisone, sulfur, menthol, pramoxine hydrochloride, and mixtures thereof being particularly preferred.

The compositions of the present invention may be directed applied to the skin or may be applied onto other delivery implements such as wipes, sponges, brushes, and the like. The compositions may be used in products designed to be left on the skin, wiped from the skin, or rinsed off of the skin.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

Vehicles/Carriers

In embodiments of the present invention related to skin and hair care compositions, the compositions of the present invention comprise a safe and effective amount of a dermatologically-acceptable carrier, suitable for topical application to the skin within which the essential materials and optional other materials are incorporated to enable the essential materials and optional components to be delivered to the skin at an appropriate concentration. The carrier can thus act as a diluent, dispersant, solvent, or the like for the active ingredients of the composition. The carrier ensures that the active ingredients of the composition can be applied to and distributed evenly over the selected target at an appropriate concentration.

The carrier can be solid, semi-solid or liquid. The carriers may be liquid or semi-solid, such as creams, lotions and gels. The carrier can itself be inert or it can possess dermatological benefits of its own. The carrier should also be physically and, chemically compatible with the essential components described herein, and should not unduly impair stability, efficacy or other use benefits associated with the compositions of the present invention.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes. The compounds which are active in the compositions and methods of this invention may be delivered topically be any means known to those of skill in the art. If the delivery parameters of the topically active pharmaceutical or cosmetic agent so require, the topically active composition may be further composed of a pharmaceutically or cosmetically acceptable vehicle capable of functioning as a delivery system to enable the penetration of the topically active agent into the skin.

The composition described herein can be prepared in the form of a cosmetic composition. The composition can be prepared in the form of basic cosmetic compositions (facial cleansers, such as toilet water, cream, essence, cleansing foam and cleansing water, pack and body oil), color cosmetic compositions (foundation, lipstick, mascara, and make-up base), hair product compositions (shampoo, rinse, hair conditioner and hair gel) and soap etc., which comprise the composition described herein as an active ingredient, together with a dermatologically acceptable carrier. The cosmetic composition can be easily prepared in any method known in the art, using the composition described herein together with at least one carrier and additives, which are commonly used in the field of preparing cosmetic compositions. Examples of cosmetic agents include emollients, humectants, colorants, pigments, fragrances, moisturizers, viscosity modifiers and any other cosmetic forming agent. One or more cosmetic agents can be included in the cosmetic composition. The form of the cosmetic composition can be a powder, lotion, gel, spray, stick cream, ointment, liquid, emulsion, foam or aerosol. In another embodiment, additional active ingredients as known in the art and described herein may also be used. Examples of the carriers may include, but are not limited to, a skin softener, a skin permeation enhancer, a colorant, an aromatic, an emulsifier, a thickener, and a solvent. Also, the cosmetic composition may further comprise a perfumery, a pigment, a bactericidal agent, an antioxidant, a preservative and a moisturizer, and also a thickener, inorganic salts and synthetic polymer substances, for the purpose of improving physical properties. Lists of such materials, and formulations for the creation of particular types of lotions, creams, sunscreens, lipsticks and other such forms are widely available in the patent literature and in commercial handbooks and can be used by those skilled in the preparation of such formulations to incorporate the composition described herein.

In one example, the facial cleanser and soap, which comprise the composition described herein, can be easily prepared by adding composition to the facial cleanser base and soap base. The cream can be prepared by adding the composition to a general oil-in-water (O/W) cream base. The cleanser, soap and cream may farther comprise a perfumery, a chelating agent, a pigment, an antioxidant and a preservative, and also synthetic or natural materials, proteins, minerals and vitamins, for the purpose of improving physical properties. Detailed descriptions of methods by which the composition may be delivered are described below. However, is should be understood that these are not limited descriptions, but merely used to illustrate possible embodiments of the invention.

Topical Delivery Via Liposomes

One acceptable vehicle for topical delivery of some of the compositions of this invention, particularly those which include proteins, may contain liposomes. The liposomes may be present in an amount, based upon the total volume of the composition, from about 10 mg/mL to about 100 mg/mL, or from about 20 mg/mL to about 50 mg/mL. The liposome may have a ratio of about 37.5:12.5:33.3:16.7. Suitable liposomes may be prepared in accordance with the protocol set forth in U.S. application Ser. No. 09/110,409, though other methods commonly used in the art are also acceptable. The above described composition may be prepared by combining the desired components in a suitable container and mixing them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 1184-88 (1995) ("Niemiec"), which is incorporated by reference herein in its entirety. We have found that the presence of these liposomes in the compositions of this invention may enhance the therapeutic capabilities of some of the compositions of this invention.

Topical Delivery Via a Solution

The topical compositions useful in the present invention can be formulated as solutions. Solutions typically include an aqueous solvent (e.g., from about 50% to about 99.99% or from about 90% to about 99% of a cosmetically acceptable aqueous solvent).

Topical Delivery Via Lotions, Creams, Emollients, or Ointments

The composition may also be delivered topically via a lotion. Lotions typically comprise from about 1% to about 20% (e.g., from about 5% to about 10%) of an emollient(s) and from about 50% to about 90% (e.g., from about 60% to about 80%) of water. Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water. Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

Creams can be made with a support that is a soap-based or fatty alcohol-based formula in the presence of an emulsifier. The soaps can be any known in the cosmetic formulation art, and include natural fatty or synthetic acids having from 12 to 20 carbon atoms (such as lauric acid, myristic acid, palmitic acid, oleic acid, stearic acid and their mixtures) in concentrations of from 10 to 30% neutralized with cosmetically acceptable salts including sodium, potassium, ammonia, monoethanolamine, triethanolamine and their mixtures.

Topical compositions useful in the subject invention may be formulated as a solution comprising an emollient. Such compositions may contain from about 2% to about 50% of an emollient(s). As used herein, "emollients" refer to materials used for the prevention or relief of dryness, as well as for the protection of the skin. When the conditioning agent is an emollient it may be selected from hydrocarbons, fatty acids, fatty alcohols and esters. Isononyl isononanoate is a hydrocarbon type of emollient conditioning agent. Other hydrocarbons that may be employed include mineral oil, polyolefins such as polydecene, and paraffins such as isohexadecane (e.g. Permethyl 99® and Permethyl 101®), Other examples of such materials are described in WO 96/16636, incorporated by reference herein. One material that may be used is known by the INCI name sucrose polycottonseedate.

Organopolysiloxane oils: The organopolysiloxane oil may be volatile, non-volatile, or a mixture of volatile and non-volatile silicones. The term "non-volatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Non-volatile polysiloxanes are preferred. Suitable silicones are disclosed in U.S. Pat. No. 5,069,897, issued Dec. 3, 1991, which is incorporated by reference herein in its entirety. Organopolysiloxanes selected from the group consisting of polyalkylsiloxanes, alkyl substituted dimethicones, dimethiconols, polyalkylaryl siloxanes, and mixtures thereof may be used. Polyalkylsiloxanes, dimethicones and cyclomethicones may be used.

Vegetable oils and hydrogenated vegetable oils: Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, partially and fully hydrogenated oils from the foregoing sources, and mixtures thereof. Animal fats and oils, e.g. cod liver oil, lanolin and derivatives thereof such as acetylated lanolin and isopropyl lanolate may be used. Also useful are $C_4$-$C_{20}$ alkyl ethers of polypropylene glycols, $C_1$-$C_{20}$ carboxylic acid esters of polypropylene glycols, and di-$C_8$-$C_{30}$ alkyl ethers, examples of which include PPG-14 butyl ether, PPG-15 stearyl ether, dioctyl ether, dodecyl octyl ether, and mixtures thereof. The compositions of the present invention may be substantially free of semi-solid hydrocarbons such as petrolatum, lanolin and lanolin derivatives, sterols (e.g., ethoxylated soya sterols), high molecular weight polybutenes and cocoa butter. By "substantially free," as used herein, means that the concentration of the semi-solid hydrocarbons are less than 10%, or less than 5% or less than 2% or 0.

$C_1$-$C_{30}$ mono- and poly-esters of sugars and related materials: These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose heptaoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 1:3 molar ratio; and the octaester of sucrose wherein the esterifying carboxylic acid moieties are laurate, linoleate and behenate in a 1:3:4 molar ratio. A solid material that may be used is sucrose polyester in which the degree of esterification is 7-8, and in which the fatty acid moieties are C18 mono- and/or di-unsaturated and behenic, in a molar ratio of unsaturates:behenic of 1:7 to 3:5. A solid sugar polyester that may be used is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

The topical compositions of the subject invention generally comprise from about 1% to about 50%, or about 3% to about 15% of a dermatologically acceptable emollient. Emollients tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, Cosmetics, Science and Technology, 2nd Edition, Vol. 1, pp. 32-43 (1972), incorporated herein by reference, contains numerous examples of materials suitable as an emollient; See also International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7 (th) Edition, 1997) (hereinafter "INCI Handbook") contains numerous examples of suitable materials. Emollients include stearyl alcohol, glyceryl monostearate, propane-1,2-diol, butane-1, 3-diol, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, polydimethylsiloxane, di-n-butyl sebacate, isopropyl myristate, isopropyl palmitate, isopropyl stearate, butyl stearate, polyethylene glycol, triethylene glycol, lanolin, sesame oil, coconut oil, arachis oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). Examples of thickening agents include cellulose derivatives (methyl cellulose and hydroxyl propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (CARBOPOLS; sold by B.F. Goodrich Company, (such polymers are described in Brown, U.S. Pat. No. 2,798,053), carboxylic acid polymers, crosslinked polyacrylates, polyacrylamides, xanthan gum and mixtures thereof. See also Sagarin, Cosmetics, Science and Technology, $2^{nd}$ Ed. Vol. 1 or INCI Handbook pp. 1693-1697. for a more complete disclosure of thickening agents or viscosity increasing agents useful herein.

Topical Delivery Via an Emulsion

The topical compositions useful in the present invention may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, INCI Handbook, pp. 1673-1686. Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Topical Delivery Via a Gel

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g. hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

Topical Delivery Via a Solid Formulation

The topical compositions of the present invention can also be formulated into a solid formulation (e.g., a wax-based stick, soap bar composition, powder, or a wipe containing liquid or powder).

The topical compositions useful in the subject invention may contain, in addition to the aforementioned components, a wide variety of additional oil-soluble materials and/or water-soluble materials conventionally used in compositions for use on skin, hair, and nails at their art-established levels.

Liquid Vehicles

Compositions can include at least one cosmetically acceptable vehicle other than water. Vehicles other than water include solids or liquids such as emollients, solvents, humectants, thickeners and powders. Suitable liquid vehicles include mineral oil, silicone oil, lipids (such as lecithin, vegetable oil, vitamin E, and derivatives of lanolin), low-molecular weight glycols such as PEG-4, PEG-6, propylene glycol, glycerine, and their lower alkyl conjugates, and ketones, such as acetone. Solvents containing unconjugated hydroxyls may undergo slow exchange with the ester groups of the polyhydroxy acids; this may affect the bulk consistency of the preparation, but would still result in slow release of the hydroxy acid monomers. Solvents include ethyl alcohol, isopropanol, ethylene glycol monoethyl ether, diethylene glycol monobutyl ether, diethylene glycol monoethyl ether, and acetone.

Additional Components

Nonlimiting examples of these additional ingredients include additional skin care actives such as peptides (e.g., Matrixyl [pentapetide derivative]), farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; sunscreens; anti-acne medicaments (resorcinol, salicylic acid, and the like; antioxidants (e.g., phytosterols, lipoic acid); flavonoids (e.g., isoflavones, phytoestrogens); skin soothing and healing agents such as *aloe* vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above-mentioned vitamin $B_3$ compounds can be incorporated as re-crystallized crystals that remain in crystallized form in the composition or as partially solubilize crystals (i.e., some of the crystals are dissolved and some remain in crystalline form in the composition.).

Various other agents may be incorporated into the composition depending on therapeutic need, desired results or for purposes of shelf-life and stability.

Pigments/Colorants

Pigments are frequently added to cosmetic formulations to achieve a desired color for application to the skin. Such pigments are known and the concentrations required to achieve a desired coloring are readily determinable. Pigments may be inorganic or organic. Inorganic pigments include iron oxides (red, black, brown colors), manganese violet, ultramarines (green, blue, pink, red, or violet aluminum sulfosilicates), aquamarines, copper powder, mica, clays, silica, and titanium dioxide. Organic dyes that have been certified by the US FDA for cosmetic use generally have the prefix "D&C" and a suffix of a color and a number (for example, D&C Green #3). There are at least 27 D&C dyes, each of which may be present as a "lake", i.e., a salt of the dye with aluminum, zirconium, strontium, barium, calcium, potassium or other metallic cations, to produce increased adherence to a substrate. In Europe, many of the same colorants, and additional colorants not approved in the U.S., are listed as "CI" dyes; for example, CI 61570 is chemically the same as D&C Green #5. Each of these pigments may further have several different trade names, or be present in mixed compositions.

Certain embodiments of the present invention contain from about 0% to about 30%, or about 1% to about 20%, or from about 2% to about 15% or from about 5% to about 15%, of a colorant, on an anhydrous pigment weight basis. These are usually aluminum, barium or calcium salts or lakes. Dyes may be present at a concentration of from about 0% to about 3% and pearlizing agents and the like from 0% to about 10%.

Colorants useful herein are all inorganic and organic colors/pigments suitable for use in cosmetic compositions. When used, pigments are typically dispersed in emollients for the good dispersion of the pigments when incorporated into lip compositions of the present invention, thus providing an even distribution of color. Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein.

Lakes suitable for use in the present invention include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue I Aluminum Lake, Red 6 Barium Lake, Red 7 Calcium Lake.

Other colors can also be included in the lipsticks, such as dyes. Suitable examples include Red 6, Red 21, Brown, Russet and Sienna dyes and mixtures thereof.

There are no specific limitations as to the pigment, colorant or filler powders used in the composition. Each may be a body pigment, inorganic white pigment, inorganic colored pigment, pearling agent, and the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, to El-Nokaly et al., issued Nov. 18, 1997, herein incorporated by reference in its entirety. These pigments and powders can be used independently or in combination.

Also useful herein are pigment and/or dye encapsulates such nanocolorants from BASF and multi-layer interference pigments such as Sicopearls from BASF.

The pigments/powders may be surface treated to provide added stability of color and ease of formulation. Hydrophobically-treated pigments may be more easily dispersed in the solvent/oil phase. In addition, it may be useful to treat the pigments with a material that is compatible with a silicone phase. Particularly useful hydrophobic pigment treatments for use in water-in-silicone emulsions include polysiloxane treatments such as those disclosed in U.S. Pat. No. 5,143,722, incorporated herein by reference in its entirety. Pigment/powders having a primary average particle size of from about 10 nm to about 100,000 nm, or about 50 nm to about 5,000 nm, or about 100 nm to about 1000 nm may be used. Mixtures of the same or different pigment/powder having different particle sizes are also useful herein (e.g., incorporating a $TiO_2$ having a primary particle size of from about 100 nm to about 400 nm with a $TiO_2$ having a primary particle size of from about 10 nm to about 50 nm).

Dispersants may also be used in conjunction with the colors and pigments of the present invention. Examples of suitable dispersants include, but are not limited to, those described in U.S. Pat. No. 5,688,493, herein incorporated by reference in its entirety.

Film-Forming Agents

Film forming agents may be optionally included in the compositions of the present invention to aid film substantivity and adhesion to the skin. Improving the long wear and non-transfer performance of the present compositions is quite desirable. Water-soluble, water insoluble, and water dispersible film forming agents can be used in the internal and external phases of the present compositions to give the desired end benefit.

The compositions may comprise from about 0% to about 20%, or from about 0.1% to about 10%, or from about 0.1% to about 5%, by weight of the composition, of the film-forming agent.

Film forming agents that may be used with the present invention include: 1) organic silicone resins, fluorinated silicone resins, copolymers of organic silicone resins, e.g., trimethylsiloxysilicate from GE (SR1000), GE's copolymers of silicone resins, e.g., SF1318 (silicone resin and an organic ester of isostearic acid copolymer) and CF1301 (silicone resin and alpha methyl styrene copolymer), Dow Corning's pressure sensitive adhesives—copolymers of silicone resins and various PDMS's (BIO-PSA series); and 2) acrylic and methacrylic polymers and resins, silicone-acrylate type copolymers and fluorinated versions of, including—silicones plus polymer SA70 from 3M, KP545 from Shin-Etsu, alkyl-acrylate copolymers, e.g., KP 561 and 562 from Shin-Etsu; 3) decene/butene copolymer from Collaborative Labs; 4) polyvinyl based materials, e.g., PVP, PVP/VA, including Antaron/Ganex from ISP (PVP/Triacontene copolymer), Luviskol materials from BASF; 5) polyurethanes, e.g., the Polyderm series from Alzo including but not limited to Polyderm PE/PA, Polyderm PPI-SI-WS, Polyderm PPI-GH, Luviset P.U.R. from BASF; 6) polyquaternium materials, e.g., Luviquat series from BASF 7) acrylates copolymers and acrylates/acrylamide copolymers, e.g., Luvimer and Ultrahold series, both available from BASF; 8) styrene-based materials; and 9) chitosan and chitosan-based materials including cellulose and cellulose-based materials. Such film formers are disclosed for example in the International Cosmetic Ingredient Dictionary and Handbook, Seventh Edition, Vol 2, 1636-1638.

Thickening Agents

The compositions of the present invention may optionally also comprise a thickening agent from about 0.1% to about 5%, or from about 0.1% to about 3%, or from about 0.25% to about 2%, of a thickening agent.

Thickening agents that may be used with the present invention include cellulose and derivatives such as cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. The material sold under the tradename Natrosol™. CS Plus from Aqualon Corporation may be used.

Other useful thickeners include *acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof. Also useful are acrylic acid/ethyl acrylate copolymers and the carboxyvinyl polymers sold by the B.F. Goodrich Company under the trade mark of Carbopol resins. Suitable Carbopol resins are described in WO98/22085.

Shine-Control Agents

Cosmetic products that improve and/or regulate the condition of the shiny appearance of skin are increasingly popular with consumers and are referred to herein as "shine-control agents." Shine control agents may be included in the compositions of the present invention.

A frequent, undesirable condition is "oily skin", which results from the excessive amount of sebum and sweat that is excreted onto the skin. Sebum is an oily mixture, composed principally of squalene, triglycerides, fatty acids and wax esters. Sebum is produced in the sebaceous glands of the skin. Oily skin is associated with a shiny, undesirable appearance and disagreeable tactile sensation. Sweat is predominantly water with trace quantities of dissolved inorganic salts such as sodium chloride and potassium chloride.

Typically, shine-control agents are porous in nature. These agents, when applied to the skin provide a reservoir to absorb excess moisture into the pores, hence reducing the visible quantity of moisture on the skin.

Absorber and non-absorbing spherical particles may be combined to provide optimum shine control as well as providing a product with the best tactile sensory performance.

Suitable shine-control agents include, but are not limited to, silicas, magnesium aluminum silicates, talc, sericite and various organic copolymers. Particularly effective shine control agents include silicates or carbonates that are formed by reaction of a carbonate or silicate with the alkali (IA) metals, alkaline earth (IIA) metals, or transition metals, and silicas (silicon dioxide). Shine control agents that may be used include calcium silicates, amorphous silicas, calcium carbonates, magnesium carbonates, zinc carbonates, and combinations thereof. Some specific examples of the silicates and carbonates useful in this present invention are more fully explained in Van Nostrand Reinhold's Encyclopedia of Chemistry, $4^{th}$ Ed. pp 155, 169, 556, and 849 (1984).

Synthetic versions of the shine-control agents, particularly silicates, may be used. Suitable synthetic carbonates are commercially available from Mallinckrodt or Whittaker, Clarke & Daniels. Examples of synthetic silicates useful in the present invention are Hubersorb 250™. or Hubersorb 600™, available from J. M. Huber.

Shine-control agents that primarily comprise silicas may be used instead of those materials comprising mainly silicates and/or carbonates when used for moisture and shine control. Silicas may also be in the form of microspheres and/or ellipsoids, as they have been found to contribute good skin feel characteristics in addition to efficient moisture absorption. Silica ellipsoids useful in the present invention are available from DuPont as ZELEC Sil and Kobo as Silica Shells. Silica microspheres are available from Kobo as MSS-500, MSS500/3, MSS-500H, MSS500/3N, MSS-500N and MSS 500/3N; Presperse as Spheron L1500, Spheron P1500. Fumed versions of silica can also be used with Aerosil from Degussa and Cab-O—Sil from Cabot both being useful.

Amongst the silicate series, magnesium aluminum silicates such as Sebumase, available from Miyoshi Kasei are useful.

When silicas, such as silica ellipsoids and silica microspheres are intended to be the main means for moisture absorption, the absorbent powder may comprise from about 1% to about 40%; or about 1% to about 25%, or about 2% to about 10%, by weight of the composition, of silicas.

Starch-based materials may also be used as shine control agents. Examples include Natrosorb W and Natrosorb HFW, DryFlo plus and DryFlo AF pure from National Starch and Chemical Company.

Skin-Conditioning Agents

Optionally, the compositions of the present invention may further comprise a skin-conditioning agent. These agents may be selected from humectants, exfoliants or emollients. Amounts of the skin-conditioning agent may range from about 0% to about 30%, or from about 1% to about 20%, or from about 1% to about 10% by weight.

Humectants

Humectants are generally substances that can attract water, usually out of the air. Humectants are generally considered to be moisturizers. Suitable humectants that can be used with the present invention include but are not limited to glycerin, sorbitol, sodium 2-pyrrolidone-5-carboxylate, soluble collagen, dibutyl phthalate, gelatin, and poly(alkylene oxide)s, such as polyethylene glycol. Sodium carbonate is used in the art as a humectant.

Desquamation Agents/Exfoliants

A safe and effective amount of a desquamation agent may be added to the compositions of the subject invention, or from about 0.1% to about 10%, or from about 0.2% to about 5%, or from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including organic hydroxy acids such as salicylic acid, glycolic acid, lactic acid, 5-octanoyl salicylic acid, hydroxyoctanoic acid, hydroxycaprylic acid, and lanolin fatty acids. One desquamation system that may be used comprises sulphydryl compounds and zwitterionic surfactants and is described in WO 96/01101, incorporated herein by reference. Another desquamation system that may be used comprises salicylic acid and zwitterionic surfactants and is described in WO 95/13048, incorporated herein by reference.

Exfoliants that may be used with the present invention include but are not limited to C2-C30 alpha-hydroxycarboxylic acids, beta-hydroxycarboxylic acids and salts of these acids. Glycolic, lactic and salicylic acids and their ammonium salts may be used. Amounts of the exfoliants may range from about 1 to about 15%, or from 2 to 10% by weight.

A wide variety of C2-C30 alpha-hydroxycarboxylic acids may be employed. Suitable examples of which include: alpha-hydroxyethanoic acid, alpha-hydroxypropanoic acid, alpha-hydroxyhexanoic acid, alpha-hydroxyoctanoic acid, alpha-hydroxydecanoic acid, alpha-hydroxydodecanoic acid, alpha-hydroxytetradecanoic acid, alpha-hydroxyhexadecanoic acid, alpha-hydroxyoctadecanoic acid, alpha-hydroxyeicosanoic acid, alpha-hydroxydocosanoic acid, alpha-hydroxyhexacosanoic acid, and alpha-hydroxyoctacosanoic acid.

Powders

Powders useful alone in dry compositions or as fillers in liquid compositions include chalk, talc, fullers earth, kaolin, starch, gums, colloidal silicon dioxide, sodium polyacrylate, tetra alkyl and/or trialkyl aryl ammonium silicate, organically modified montmorillonite clay, hydrated aluminum silicate, fumed silica, carboxyvinyl polymer, and sodium carboxymethyl cellulose.

Gels

Cosmetic gels may contain thickening or gelling agents such as sodium alginate or arabic gum or cellulose derivatives optionally in the presence of a solvent. The thickening agent concentration may range from about 0.5 to about 30 weight percent or from about 0.5 to about 15 weight percent. Solvents used can be aliphatic lower alcohols, glycols and their ethers with the concentration of the solvents ranging from about 2 to about 20%.

Solidifying Agents

The cosmetic compositions of this invention may also contain one or more materials, herein singly or collectively referred to as a "solidifying agent," that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition that has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent may be present at a concentration of from about 0 to about 90%, or from about 1 to about 50%, or from about 5% to about 40%, or from about 1% to about 15%.

Suitable solidifying agents may include waxy materials such as candelilla, carnauba, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40-1.42, herein incorporated by reference.

Spray Propellants

Spray compositions may require propellants, including propane, butane, isobutane, carbon dioxide, and nitrous oxide.

Fragrances

The composition can also include a perfume in an amount sufficient to make the composition acceptable to the consumer and pleasant to use. Usually, the perfume will form from about 0.01% to about 10% by weight of the composition.

Surfactants

Compositions herein may contain an emulsifier and/or surfactant, generally to help disperse and suspend the discontinuous phase within the continuous phase. A surfactant may also be useful if the product is intended for skin cleansing. For convenience hereinafter emulsifiers will be referred to under the term "surfactants", thus "surfactant(s)" will be used to refer to surface active agents whether used as emulsifiers or for other surfactant purposes such as skin cleansing. Known or conventional surfactants can be used in the composition, provided that the selected agent is chemically and physically compatible with essential components of the composition, and provides the desired characteristics. Suitable surfactants include silicone materials, non-silicone materials, and mixtures thereof.

The compositions of the present invention may comprise from about 0.05% to about 15% of a surfactant or mixture of surfactants. The exact surfactant or surfactant mixture chosen will depend upon the pH of the composition and the other components present. Surface active agents (detergents) useful in cosmetic compositions include anionic surface active agents, such as salts of fatty acids (for example, sodium laurate and triethanolamine oleate), alkyl benzene sulfonates (such as triethanolamine dodecyl benzene sulfonate), alkyl sulfates such as sodium lauryl sulfate, alkyl ether sulfates, monoglyceride sulfates, isethionates, methyl taurides, acylsarcosinates, acyl peptides, acyl lactylates, polyalkoxylated ether glycolates, for example trideceth-7 carboxylic acid, and phosphates such as sodium dilauryl phosphate. Amphoteric surface active agents include imidazole compounds, N-alkyl amino acids, (such as sodium cocaminopropionate and asparagine derivatives), and betaines. Nonionic surface active agents, such as fatty acid alkanolamides, for example, oleic ethanolamide; esters of polyalcohols, for example Span; polyglycerol esters; polyalkoxylated derivatives, for example TRITON X-100™, polyoxyethylene lauryl ether, and TWEEN™; and amine oxides, such as dodecyl dimethyl amine oxides. Cationic surfactants may be of use in the composition. Mixtures of two or more of the above surface active agents can be employed in the composition. As noted above, many surfactants may also be used for their functionality as emollients, humectants or vehicles.

Other useful nonionic surfactants include the condensation products of alkylene oxides with fatty acids (i.e. alkylene oxide esters of fatty acids). These materials have the general formula $RCO(X)_n OH$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_n OOCR$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_n OR'$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_n OR'$ wherein R and R' are $C_{10-30}$ alkyl groups, X is $—OCH_2CH_2$ (i.e. derived from ethylene glycol or oxide) or $—OCH_2CHCH_3—$(derived from propylene glycol or oxide), and n is an integer from about 6 to about 100, examples of which include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants, which are described in more detail in WO 98/04241.

Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, and mixtures thereof. Examples of these non-silicon-containing surfactants include: polysorbate 20, polyethylene glycol 5 soya sterol, steareth-20, ceteareth-20, PPG-2 methyl glucose ether distearate, ceteth-10, polysorbate 80, polysorbate 60, glyceryl stearate, sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Sunscreen

The composition may include an effective amount of a sunscreen agent to provide protection from the harmful effects of excessive exposure to sunlight. This can be particularly important when the skin is partially debrided by the application of a hydroxy acid. Examples of suitable organic sunscreens, when required, include Benzophenone-3, DEA Methoxycinnamate, Ethyl dihydroxypropyl PABA, Glyceryl PABA, Octyl methoxycinnamate, Octyl salicylate, 2-phenyl-benzimidazole-5-sulfonic acid, and Butyl methoxy dibenzoylmethane. An inorganic sunscreen, such as titanium dioxide or zinc oxide, can also be used. The sunscreen ingredients may be present free in the formulation. The organic sunscreens may also be coupled to the conjugate block copolymer, as described above.

Anti-Oxidants

Anti-oxidants/radical scavengers such as ascorbic acid (vitamin C) and its salts, ascorbyl esters of fatty acids, ascorbic acid derivatives (e.g., magnesium ascorbyl phosphate), beta-carotene, tocopherol (vitamin E), tocopherol sorbate, tocopherol acetate, other esters of tocopherol, butylated hydroxy benzoic acids and their salts, gallic acid and its alkyl esters, such as propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, bioflavonoids, lysine, methionine, proline, superoxide dismutase, silymarin, tea extracts, grape skin/seed extracts, melanin, and rosemary extracts may be used. Anti-oxidants/radical scavengers that may be used include tocopherol acetate, tocopherol sorbate and other esters of tocopherol.

The tocopherol (vitamin E group) used as an additive or as an antioxidant for retinol, or a derivative, when present in the composition may include alpha-tocopherol, beta-tocopherol, gamma-tocopherol, and delta-tocopherol. The amount of tocopherol, when present in the composition, may be from about 0.0001 to about 50%, or from about 0.001 to about 10% by weight of the composition.

Chelators

The composition may also further comprises biofilm dislodging enhancer agents such as chaotropic agents or calcium chelators.

The inclusion of a chelating agent is useful for providing protection against UV radiation which can contribute to excessive scaling or skin texture changes and against other environmental agents which can cause skin damage. A suitable amount is from about 0.01% to about 1%, or from about 0.05% to about 0.5%, of the composition. Exemplary chelators that are useful herein are disclosed in U.S. Pat. No. 5,487,884, incorporated herein by reference. Chelators that may be useful in compositions of the subject invention are ethylenediamine tetraacetic acid (EDTA), furildioxime and derivatives thereof.

A calcium chelator such as EDTA, may also be in a salt form, in a concentration of at least about 0.25%, or any calcium chelator having a chelating potency substantially equivalent thereto may be added.

Skin-Lightening Agents

The compositions of the present invention can also comprise a skin lightening agent. When used, the compositions may comprise from about 0.1% to about 10%, or from about 0.2% to about 5%, or from about 0.5% to about 2%, of a skin lightening agent. Suitable skin lightening agents include those known in the art, including kojic acid, arbutin, ascorbic acid and derivatives thereof, e.g., magnesium ascorbyl phosphate. Further skin lightening agents suitable for use herein also include those described in WO 95/34280 and WO 95/23780; each incorporated herein by reference.

Anti-Aging Additives

The composition can also include an additional anti-aging active such as retinol (Vitamin A) and/or derivative thereof, to enhance repair of photodamage to skin following exposure to ultra-violet light. In addition to retinol itself, examples of derivatives of retinol include: Retinyl acetate, Retinyl butyrate, Retinyl propionate, Retinyl octanoate, Retinyl laurate, Retinyl palmitate, Retinyl oleate, and Retinyl linoleate. The amount of retinol, or a cosmetically acceptable derivative thereof, when present in the composition is from about 0.01 to about 10% or from about 0.1 to about 5% by weight of the composition. The retinols or derivatives may be coupled to the conjugate. Estradiol, estriol, hyaluronic acid, and green tea extract may be incorporated into anti-wrinkle skin cleaning or moisturizing compositions. These formulations may also have ascorbic acid, date palm extract or combinations thereof.

Particulate Material

Particulate materials, including both organic and inorganic particles, have been included in skin care compositions. See, for example, "Quantification of the Soft-Focus Effect," Cosmetics & Toiletries, Vol. 111, July 1996, pp. 57-61, which discloses that one can physically fill in skin lines with a reflective substance such as $TiO_2$. Compositions within the scope of the present invention may include particulate materials according to methods and materials described in U.S. Pat. No. 4,892,726, issued to Toshiba Silicone Co. Ltd. Compositions including particulate materials such as polymethylsilsesquioxane powders in makeup and cosmetic compositions are smooth upon application and impart natural colour. An example of such a particle is Tospearl®, available from Toshiba Silicone Co. Ltd. U.S. Pat. No. 5,223,559 describes the use of a variety of particulate fillers of particle size from 0.5 to 50 μm, particularly from 1 to 15 μm, for blurring skin defects.

Particulate materials may have a neat primary particle size of from about 2 to about 15 μm, or from about 2 to about 10 μm, or from about 3 to about 7.5 μm. Median particle size can be determined by any suitable method known in the art, such as by using coulter-counter equipment or the ASTM Designation E20-85 "Standard Practice for Particle Size Analysis of Particulate Substances in the Range of 0.2 to 75 Micrometers by Optical Microscopy," ASTM Volume 14.02, 1993, incorporated herein by reference.

The particulate materials can be inorganic or organic, such as organosilicone, or organosilicone polymers. Particles may be free-flowing, solid, materials. By "solid" is meant that the particles are not hollow. The void at the centre of hollow particles can have an adverse effect on refractive index and therefore the visual effects of the particles on either skin or the composition.

A representative commercially available example of a particulate material is Tospearl®145 which has a median particle size of about 4.5 μm. A further representative commercially available example is Orgasol®2002 D NAT COS available from Elf Atochem SA, Paris, France, which is an example of a polyamide organic particulate material. A representative commercially available example of the second particulate material is EA-209® from Kobo which is an ethylene/acrylic acid copolymer having a median particle size of about 10 μm. Other particulate materials that may be used are those made of polymethylsilsesquioxane, referenced above, polyamide, polythene, polyacrylonitrile, polyacrylic acid, polymethacrylic acid, polystyrene, polytetrafluoroethylene (PTFE) and poly(vinylidene chloride). Copolymers derived from monomers of the aforementioned materials can also be used. Inorganic materials include silica and boron nitride.

The compositions of the present invention may comprise one or more particulate materials in a concentration of from about 0.5% to about 25%, or from about 1% to about 20%, or from about 2% to about 12%.

Other Additives

The composition can also contain adjuncts conventionally used in skin-treating compositions other than those already mentioned, depending on the form of the intended product. It is, for example, possible to include antiseptics, preservatives, and coloring agents, which can improve the stability and consumer appeal of the composition. Examples of other materials include anti-microbials including bactericides and fungicides, acne medication, and wart removers including salicylic acid. Agents known in the art for treatments of conditions such as blisters, insect bites, diaper rash and canker sores may be included; these may be include local anesthetics, emollients, and other known materials.

pH-Adjusting Agents

The use of one or more pH-adjusting agents, including minor amounts of mineral acids, basic compositions, and organic acids may be used. An exemplary composition includes citric acid, such as is available in an anhydrous salt form of an alkali metal citric acid. The addition of an effective amount of such a pH-adjusting agent is useful in establishing a targeted pH range for compositions according to the invention. The addition of an effective amount of a pH buffering composition so as to maintain the pH of the inventive compositions may also be added. The pH of the final composition is about 4 to about 8, or about 5 to about 7.

Examples of such useful pH buffer compounds and/or pH buffering systems or compositions are alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, citrates, and their alkali metal salts. Such buffers keep the pH ranges of the compositions of the present invention within acceptable limits. Others, not particularly elucidated here may also be used. Citric acid, such as is available in an anhydrous salt form of an alkali metal citric acid may be added as it is readily commercially available, and effective. The addition of such a buffering agent is desirable in certain cases wherein long term, i.e., prolonged storage, is to be anticipated for a composition, as well as insuring the safe handling of the aqueous composition.

Preservatives

Suitable traditional preservatives for compositions of this invention are alkyl esters of parahydroxybenzoic acid. Other preservatives that have more recently come into use include hydantoin derivatives such as 1,3-bis(hydroxymethyl)-5,5-dimethylhydantoin, propionate salts, and a variety of quaternary ammonium compounds such as benzalkonium chloride, quaternium 15 (Dowicil 200), benzethonium chloride, and methylbenzethonium chloride. Cosmetic chemists are familiar with appropriate preservatives and routinely choose them to satisfy the preservative challenge test and to provide product stability. Disodium EDTA, phenoxyethanol, methyl paraben, propyl paraben, imidazolidinyl urea (commercially available as Germall 1157), sodium dehydroacetate or benzyl alcohol may be used with the present invention. The preservatives should be selected having regard for the use of the composition and possible incompatibilities between the preservatives and other ingredients in the emulsion. Preservatives are employed in amounts ranging from about 0% to about 5%, or from about 0.01% to about 2.5%, or from about 0.01% to about 1%, by weight of the composition.

Water

Where necessary, the compositions further include water sufficient to provide the remaining weight of the composition. Deionized or distilled water may be employed.

Additional Active Agents that May be Used with the Present Invention

Ingredients that Alleviate Psoriasis

The present invention may also include active agents that alleviate psoriasis. Such agents should be those that are acceptable for topical application. These agents are known to those of skill in the art. Examples of antipsoriatic agents include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionate, flurandrenolide, mometasone furoate, and methylprednisolone acetate), methotrexate, cyclosporine, calcipotriene, anthraline, shale oil, elubiol, ketoconazole, coal tar, salicylic acid, zinc pyrithione, selenium sulfide, hydrocortisone, sulfur, menthol, and pramoxine hydrochloride, and combinations thereof. In one embodiment, the compositions of the present invention include an anti-viral agent. Examples of anti-viral agents include, but are not limited to, imiquimod, podofilox, podophyllin, interferon alpha, acyclovir, famcyclovir, valcyclovir, reticulos and cidofovir.

Antimicrobial Agents

In one embodiment, the compositions of the present invention include an antimicrobial agent. "Antimicrobial agent" as used herein is a compound that kills microorganisms or prevents or inhibits their growth or reproduction. Examples of antimicrobial agents include, but are not limited to ethanol, propanol, betains, benzalkonium chloride, benzethonium chloride, lauric arginayte, sugarquat, methyl benzethonium chloride, cetypyridiunium chloride, 2,4,4',-trichloro-2-hydroxydiphenyl ether (Triclosan), parachloro-meta xylenol (PCMX), Iodopropynyl butylcarbamate, diazolidinyl urea, chlorhexidene digluconate, chlorhexidene acetate, chlorhexidene isethionate, chlorhexidene hydrochloride, hexetidine, Quaternium 15, triclocarbon, polyhexamethylene biguanide, cetylpyridium chloride, imidazolidinyl urea, diazolidinyl urea, 3-iodo-2-propynyl-N-butylcarbamate, 2-methyl-4-isothiazolin-3-one, dimethyl dimethyl hydan-toin, (5-chloro-2-(2,4-dichlorophenoxy) phenol, monolaurin glyceryl laurate, *camellia sinensis, candida bombi-cola*/glucose/methyl rapeseedate ferment, hydrogen peroxide, phenol, poloxamer 188, PVP-iodine, thiourea, natural antimicrobial agents, such as cinnamon oil, cinnamaldehyde, lemongrass oil, clove oil, saw palmetto extract, thyme oil white, thyme oil red, thymol, tea tree oil, *pinus pinaster* bark extract, rosemary leaf extract, grape seed extract, and betel oil, silver containing compounds, such as silver nitrate, silver lactate, silver citrate, and silver zeolite, antimicrobial fatty acid ester of a polyhydric alcohol, a fatty ether of a polyhydric alcohol and alkoxylated derivatives thereof, and combinations thereof.

Bactericidal agents used in the present invention may include enzymatic enzymes. These may include any member from the class of oxido-reductases, EC 1 that generate active oxygen; Monosaccharide oxidases, Peroxidases, Lactoperoxidases, Salivary peroxidases, Myeloperoxidases, Phenol oxidase, Cytochrome oxidase, Dioxygenases, Monooxygenases. The enzymes also include bacterial cell lytic enzymes, e.g., Lysozyme, Lactoferrin. Other agents include antimicrobials e.g., chlorhexidine, amine fluoride compounds, fluoride ions, hypochlorite, quaternary ammonium compounds e.g. cetylpyridinium chloride, hydrogen peroxide, monochloramine, povidone iodine, any recognized sanitizing agent or oxidative agent and biocides.

Compositions of the present invention may also include antibiotics including, but not limited to the following classes and members within a class: Aminoglycosides: Gentamicin, Tobramycin, Netilmicin, Amikacin, Kanamycin, Streptomycin, Neomycin; Quinolones/Fluoroquinolones: Nalidixic Acid, Cinoxacin, Norfloxacin, Ciprofloxacin, Perfloxacin, Ofloxacin, Enoxacin, Fleroxacin, Levofloxacin; Antipseudomonal: Carbenicillin, Carbenicillin Indanyl, Ticarcillin, Azlocillin, Mezlocillin, Piperacillin; Cephalosporins: Cephalothin, Cephaprin, Cephalexin, Cephradine, Cefadroxil, Cefazolin, Cefamandole, Cefoxitin, Cefaclor, Cefuroxime, Cefotetan, Ceforanide, Cefuroxine Axetil, Cefonicid, Cefotaxime, Moxalactam, Ceftizoxime, Ceftriaxone, Cefoperazone, Cftazidime, Cephaloridine, Cefsulodin; Other beta-Lactam Antibiotics: Imipenem, Aztreonam; beta-Lactamase Inhibitors: Clavulanic Acid, Augmentin, Sulbactam; Sulfonamides: Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole; Urinary Tract Antiseptics Methenamine, Nitrofurantoin, Pheniazopyridine and other napthpyridines; Penicillins: Penicillin G and Penicillin V; Penicillinase Resistant: Methicillin, Nafcillin, Oxacillin, Cloxacillin, Dicloxacillin; Penicillins for Gram-Negative/Amino Penicillins: Ampicillin (Polymycin), Amoxicillin, Cyclacillin, Bacampicillin; Tetracyclines: Tetracycline, Chlortetracycline, Demeclocycline, Methacycline, Doxycycline, Minocycline; Other Antibiotics Chloramphenicol (Chlormycetin), Erythromycin, Lincomycin, Clindamycin, Spectinomycin, Polymyxin B (Colistin), Vancomycin, Bacitracin; Tuberculosis Drugs: Isoniazid, Rifampin, Ethambutol, Pyrazinamide, Ethinoamide, Aminosalicylic Acid, Cycloserine; Anti-Fungal Agents: Amphotericin B, Cyclosporine, Flucytosine; Imidazoles and Triazoles: Ketoconazole, Miconazole, Itraconazole, Fluconazole, Griseofulvin; Topical Anti Fungal Agents: Clotrimazole, Econazole, Miconazole, Terconazole, Butoconazole, Oxiconazole, Sulconazole, Ciclopirox Olamine, Haloprogin, Tolnaftate, Naftifine, Polyene, Amphotericin B, Natamycin In one embodiment, the amount of antimicrobial agent in the compositions is from about 0.001% to about 10%, such as from about 0.01% to about 5%, such as from about 0.05% to about 2% by weight, based on the total weight of the composition.

In one embodiment the antimicrobial agent is an anti-fungal agent such as an azole. Examples include, but are not limited to, miconazole, ketoconazole, econazole, itraconazole, sertaconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, their cosmetically acceptable salts, and combinations thereof. In one embodiment the antimicrobial agent is an antibiotic or an antiseptic. Examples include, but are not limited to, mupirocin, neomycin sulfate bacitracin, polymyxin B, 1-ofloxacin, tetracyclines such as chlortetracycline hydrochloride, oxytetracycline-10 hydrochloride and tetrachcy-cline hydrochloride, clindamycin phosphate, gentamicin sulfate, metronidazole, hexylresorcinol, methylbenzethonium chloride, phenol, quaternary ammonium compounds, tea tree oil, and combinations thereof.

Anti-Inflammatory Agents

In another embodiment, the compositions of the present invention may include an anti-inflammatory agent. A safe and effective amount of an anti-inflammatory agent may be added to the compositions of the subject invention, from about 0.1% to about 5%, or from about 0.1% to about 2%, of the composition. The anti-inflammatory agent enhances the skin appearance benefits of the present invention, e.g., such agents contribute to a more uniform and acceptable skin tone or colour. The exact amount of anti-inflammatory agent to be used in the compositions will depend on the particular anti-inflammatory agent utilized since such agents vary widely in potency.

Anti-inflammatory agents useful herein include steroids such as hydrocortisone; panthenol and ether and ester derivatives thereof e.g. panthenol ethyl ether, panthenyl triacetate; pantothenic acid and salt and ester derivatives thereof, such as calcium pantothenate; *aloe* vera, bisabolol, allantoin and compounds of the liquorice (the plant genus/species *Glycyrrhiza glabra*) family, including glycyrrhetic acid, glycyrrhizic acid, and derivatives thereof e.g. salts such as ammonium glycyrrhizinate and esters such as stearyl glycyrrhetinate. Suitable levels may be from about 0.1 to about 5%, or from about 0.5 to about 3%. Additional anti-inflammatory agents include, but are not limited to, corticosteroids such as hydrocortisone, hydroxyltriamcinolone alphamethyl dexamethasone, dexamethasone-phosphate, beclomethasone dipropionate, clobe-tasol valerate, desonide, desoxymethasone, deoxycorticosterone acetate, dexamethasone, dichlorisone, diflorasone diacetate, diflucortolone valerate, fluadrenolone, fluclarolone acetonide, fludrocortisone, flumethasone pivalate, fluosi-nolone acetonide, fluocinonide, flucortine butylester, fluocortolone, fluprednidene (fluprednylidene)acetate, flurandre-nolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortolone, clescinolone, dichlorisone, difluprednate, fluclorinide, flunisolide, fluorometholone, fluperolone, fluprednisolone, hydrocortisone valerate, hydro-cortisone cyclopentylproprionate, hydrocortamate, meprednisone, paramethasone, prednisolone, prednisone, beclomethasone dipropionate, betamethasone dipropionate, and triamcinolone, and combinations thereof.

Other active agents that may be incorporated into embodiments of the present invention include, but are not limited to, wound healing enhancing agents such as calcium alginate, collagen, recombinant human platelet-derived growth factor (PDGF) and other growth factors, ketanserin, iloprost, prostaglandin E1 and hyaluronic acid; scar reducing agents such as mannose-6-phosphate; analgesic agents; debriding agents such as papain, and enzymatic debriding agents; and anesthetics such as lidocaine and benzocaine. In one embodiment, the composition comprises one or more of menthol, camphor, an antihistamine, or a local anesthetic such as tetracaine, lidocaine, prilocaine, benzocaine, bupivacaine, mepivacaine, dibucaine, etidocaine, butacaine, cyclomethycaine, hexylcaine, proparacaine, and lopivacaine, capsaicin, or oatmeal.

In one embodiment, the amount of anti-inflammatory agent, anti-viral agent, anti-psoriatic agent and/or other active agent in the compositions is from about 0.001% to about 10%, such as from about 0.01% to about 5% such as from about 0.05% to about 2% by weight, based on the total weight of the composition.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present invention are useful for regulating mammalian skin condition, for example human skin, including the face, scalp, and hands or other non-facial parts of the body, including regulating visible and/or tactile discontinuities in skin, e.g., visible and/or tactile discontinuities in skin texture, such as discontinuities associated with skin ageing. Regulating skin condition involves topically applying to the skin a safe and effective amount of a composition of the present invention. The amount of the composition which is applied, the frequency of application and the period of use will vary widely depending upon the active levels of a given composition and the level of regulation desired, e.g., in light of the level of skin ageing present in the subject and the rate of further skin ageing.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 2 mg/cm$^2$. Typically applications would be on the order of about once per day, however application rates can vary from about once per week up to about three times per day or more.

The compositions of this invention provide a visible improvement in skin condition essentially immediately following application of the composition to the skin. Such immediate improvement involves coverage or masking of skin imperfections such as textural discontinuities (including those associated with skin ageing, such as enlarged pores), and/or providing a more even skin tone or color.

The compositions of the invention also provide visible improvements in skin condition following chronic topical application of the composition. "Chronic topical application" and the like involves continued topical application of the composition over an extended period during the subject's lifetime, for a period of at least about one week, or for a period of at least about one month, or for at least about three months, or for at least about six months, or for at least about one year. Chronic regulation of skin condition involves improvement of skin condition following multiple topical applications of the composition to the skin. Typically applications would be on the order of about once per day over such extended periods, however application rates can vary from about once per week up to about three times per day or more.

Regulating skin condition may be practiced by applying a composition in the form of a skin lotion, cream, cosmetic, or the like which is intended to be left on the skin for an extended period for some aesthetic, prophylactic, therapeutic or other benefit (i.e., a "leave-on" composition). As used herein, "leave-on" compositions exclude rinse-off skin cleansing products. After applying the composition to the skin, the leave-on composition is may be left on the skin for a period of at least about 15 minutes, or at least about 30 minutes, or at least about 1 hour, or for at least several hours, e.g., up to about 12 hours.

EXAMPLES

The compositions of the present invention are generally prepared by conventional methods such as are known in the art of making topical compositions. Such methods typically involve mixing of the ingredients in one or more steps to a relatively uniform state, with or without heating, cooling, application of vacuum and the like.

The following examples further describe and demonstrate embodiments within the scope of the present invention. The examples are given solely for the purpose of illustration and are not to be construed as limitations of the present invention.

Example 1

Oil-in-Water Emulsions

The following emulsion is prepared using conventional formulating techniques.

|  | 1% w/w | 2% w/w | 3% w/w |
| --- | --- | --- | --- |
| Meta Silicate | 0.21 | 0.31 | 0.42 |
| Sodium Carbonate | 0.16 | 0.22 | 0.32 |
| Sodium Glyconate | 0.06 | 0.09 | 0.13 |
| Potassium Aluminum Sulfate | 0.06 | 0.09 | 0.13 |
| Tospearl ® 145 | 6.0 | 9.0 | 3.0 |
| Polyacrylamide (thickening agent) | 2.0 | 2.0 | 1.0 |
| Xanthan Gum (thickening agent) |  | 0.6 | 0.3 |
| Glycerine (plasticizing agent/humectant) | 7.0 | 5.0 | 3.0 |
| Urea (antimicrobial) | 0.0 | 0.0 | 2.0 |
| Panthenol (hair conditioning agent) | 1.0 | 0.0 | 0.0 |
| Salicylic acid (anti-acne agent) | 0.0 | 1.5 | 0.0 |
| Allantoin (anti-inflammatory agent) | 0.2 | 0.1 | 0.0 |
| Aloe Vera gel (anti-inflammatory) | 0.0 | 0.0 | 0.05 |
| Tocopheryl acetate | 0.0 | 0.0 | 0.05 |
| Cetyl Alcohol (emollient) | 2.0 | 1.0 | 1.25 |
| Stearyl alcohol (emollient) | 2.0 | 1.0 | 1.25 |
| Cyclomethicone (emollient) and dimethiconol | 0.75 | 0.5 | 0.50 |
| Steareth-21 (surfactant) | 0.6 | 0.4 | 0.3 |
| Steareth-2 (surfactant) | 0.1 | 0.08 | 0.03 |
| Sorbitan stearate & sucrose cocoate (surfactants) | 1.5 | 0 | 0 |
| PPG-15 stearyl ether (emollient) | 3.0 | 5.0 | 4.0 |
| Sucrose polycottonseedate (emollient) | 2.0 | 3.0 | 0 |
| Dimethicone (silicone conditioning agent) | 0.5 | 0 | 0 |
| Disodium EDTA | 0.02 | 0.01 | 0.02 |
| Deionized water | To 100% | To 100% | To 100% |

Example 2

Moisturizing Lotion

| | |
| --- | --- |
| Meta Silicate | 0.31 |
| Sodium Carbonate | 0.22 |
| Sodium Glyconate | 0.09 |
| Potassium Aluminum Sulfate | 0.09 |
| Cyclomethicone (emollient) | 17.35 |
| Propylparaben (preservative) | 0.20 |
| Ethylene/Acrylic Acid Copolymer microspheres (e.g., Flobeads EA 209 supplied by Kobo Products) | 10.0 |
| Glycerin (plasticizing agent/humectant) | 25.00 |
| Niacinamide (Vitamin B$_3$) | 3.00 |
| Methylparaben (preservative) | 0.12 |
| Water | to 100% |

In a suitable vessel, the meta silicate, sodium carbonate, sodium glyconate, potassium Al sulfate are mixed with the niacinamide and water until homogeneous. To this mixture is added the glycerin, ethylene/acrylic acid copolymer microspheres and methylparaben with mixing until homogenous. The Mixture is then combined with the cyclomethicone and mixed using conventional mixing methods until homogenous. The mixture is then poured into suitable containers. The moisturizing cosmetic lotion is applied to the face and/or body to provide softening, moisturization and conditioning.

Example 3

Liquid Foundation

| | |
| --- | --- |
| Meta Silicate | 0.31 |
| Sodium Carbonate | 0.22 |
| Sodium Glyconate | 0.09 |
| Sea salt | 0.09 |
| Cyclomethicone | 11.62 |
| Dimethicone copolyol emulsifier | 0.7 |
| Isononyl isononanoate (emollient) | 5.00 |
| n-propyl-4-hydroxybenzoic acid (anti-fungal/preservative) | 0.20 |
| Fragrance | 0.03 |
| Titanium dioxide (pigment/sunscreen) | 17.8 |
| Yellow iron oxide (pigment) | 1.70 |
| Red iron oxide (pigment) | 0.19 |
| Black iron oxide (pigment) | 0.11 |
| Methylparahydroxybenzoate (preservative) | 0.12 |
| Glycerin | 10.0 |
| 2-amino-2-methyl-1-propanol | 0.10 |
| Sucrose oleate ester (emollient) | 0.60 |
| water | to 100% |

Hair Care Products

In one embodiment, the present invention relates to hair care compositions, particularly those that contact the scalp. In one embodiment, the present invention may be used to alleviate or improve dandruff or other conditions of the scalp. In yet another embodiment, the composition may also include active ingredients known to improve dandruff or similar conditions of the scalp.

The composition of the present invention may be incorporated into hair care products, such as shampoos, conditioners, styling products and hair coloring products, as known and described in the art. The present composition is particularly useful for the treatment of dandruff or other conditions that affect the scalp.

In this embodiment, the composition comprises meta silicate, carbonate glyconate, and aluminum sulfate in a suitable carrier for treatment of the hair and scalp. The composition may comprise a) from about 0.04% to about 1.6% of a meta silicate, b) from about 0.03% to about 1.2% of a carbonate, c) from about 0.01% to about 0.04% of a glyconate, and d) from about 0.01% to about 0.04% of a sulfate.

The composition may be delivered to the scalp and hair in the form of a shampoo, conditioner, styling product or other liquid or cream formulation that may be formulated as known in the art. See, for example, U.S. Pat. No. 5,883,058, Wells, et al.; U.S. Pat. No. 5,837,661, Evans, et al.

The present composition can be used to produce sprayable, pumpable, and foamable, non-aerosol gels and foams, such as sprayable hair gels and foamable sun protection products with optimized spray pattern and optimized droplet size distribution. These compositions may be directly applied to the scalp to treat dandruff or similar conditions, or the compositions may be applied to the scalp and hair simultaneously.

Optional Ingredients

Non-limiting examples of optional components for use in the shampoo composition include particles, cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, and vitamins.

Additionally, Pigments or coloring agents, opacifiers, pearlescent agents, feel modifiers, oil absorbers, skin protectants, matting agents, friction enhancers, slip agents, conditioning agents, exfoliants, odor absorbers, or cleaning enhancers may be added to the hair care formulation.

Other active ingredients useful as treatment agents for various disorders or conditions may also be added to the hair care composition, including antiperspirant agents, anti-dandruff agents, antimicrobials, antibiotics, and sunscreens. The shampoo compositions may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the shampoo compositions.

Silicone Conditioning Agent

The compositions of the present invention may optionally include a silicone conditioning component. The silicone conditioning component may comprise volatile silicone, nonvolatile silicone, or mixtures thereof. As used herein, "nonvolatile" refers to silicone material with little or no significant vapour pressure under ambient conditions, as is understood by those in the art.

The compositions of the invention can contain emulsified droplets of a silicone conditioning agent, for enhancing conditioning performance.

Suitable silicones include polydiorganosiloxanes, in particular polydimethylsiloxanes that have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) may be at least 10,000 cst at 25° C. the viscosity of the silicone itself is preferably at least 60,000 cst, most preferably at least 500,000 cst, ideally at least 1,000,000 cst.

Emulsified silicones for use in the shampoo compositions of the invention may have an average silicone droplet size in the composition of less than 30, preferably less than 20, more preferably less than 10 µm, ideally from 0.01 to 1 µm. Silicone emulsions having an average silicone droplet size of <0.15 µm are generally termed microemulsions.

Examples of pre-formed emulsions include emulsions DC2-1766, DC2-1784, DC-1785 DC-1786 and microemulsions DC2-1865 and DC2-1870, all available from Dow Corning. These are all emulsions/microemulsions of dimethiconol. Cross-linked silicone gums are also available in a pre-emulsified form, which can be advantageous for ease of formulation. DC X2-1787, which is an emulsion of cross-linked dimethiconol gum or DC X2-1391, which is a microemulsion of cross-linked dimethiconol gum, may both be used with the present invention and are available from Dow Corning.

A further class of silicones that may be included in embodiments of the present invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone", Specific examples of amino functional silicones suitable for use in the invention are the aminosilicone oils DC2-8220, DC2-8166, DC2-8466, and DC2-8950-114 (all ex Dow Corning), and GE 1149-75. Suitable quaternary silicone polymers are described in EP-A-0 530 974. An example of a quaternary silicone polymer is K3474.

Also suitable are emulsions of amino functional silicone oils with non-ionic and/or cationic surfactant. Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning). With some shampoos a combination of amino and non amino functional silicones may be used.

The total amount of silicone may be from about 0.01 to about 10% wt of the total composition or from about 0.3 to about 5; or from about 0.5 to about 3-wt % is a suitable level.

Cationic Conditioning Agents

The compositions of the present invention can also comprise one or more additional cationic polymeric conditioning agents such as those known with their CTFA category name of Polyquaternium. Typical examples are Polyquaternium 6, Polyquaternium 7, Polyquaternium 10, Polyquaternium 11, Polyquaternium 16, Polyquaternium 22 and Polyquaternium 28. Quaternium polymers may also be used. These include Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84. Cationic cellulose type polymers known as Polymer JR type from Amerchol such as Polyquaternium 10 or cationic guar gum known with trade name Jaguar from Rhone-Poulenc and chemically for example Guar hydroxypropyl trimonium chloride, may also be used. Chitosan and chitin can also be included in the compositions as cationic natural polymers. The cationic polymers may also include the quaternized products of graft polymers from organopolysiloxanes and polyethyl oxazolines. Formulations using these polymers are described in US Application 20060140887, Molenda, et al. It is also possible to use mixtures of various cationic polymers.

The cationic polymer conditioning agents may be water soluble. The total level of cationic polymers in the compositions of the present invention may be from about 0.001% to about 20%, or from about 0.005% to about 10%, or from about 0.01% to about 2%, by weight.

Non-Silicone Oily Conditioning Components

Compositions according to the present invention may also comprise a dispersed, non-volatile, water-insoluble oily conditioning agent.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof. Straight chain hydrocarbon oils may contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, or at least 20. Di- and trialkyl and alkenyl esters of carboxylic acids can also be used.

Fatty esters that may be used with the present invention may be mono-, di- and triglycerides, more specifically the mono-, di-, and trimesters of glycerol and long chain carboxylic acids such as $C_1$-$C_{22}$ carboxylic acids. Materials that may be used include cocoa butter, palm stearin, sunflower oil, soybean oil and coconut oil.

The oily or fatty material is suitably present at a level of from about 0.05 to about 10, or from about 0.2 to about 5, or from about 0.5 to about 3 wt %.

In hair treatment compositions containing a conditioning agent, a cationic polymer may also be present.

Sensates

The hair care compositions of the present invention may also comprise a sensate. As used herein the term "sensate" means a substance that, when applied to the skin, causes a perceived sensation of a change in conditions, for example, but not limited to, heating, cooling, refreshing and the like.

Any sensate suitable for use in hair care compositions may be used herein. Use of sensates are described in U.S. Application 20010043912, Michael et al. incorporated by reference herein. Examples of sensates that can be used in the compositions herein are camphor, menthol, 1-isopulegol, ethyl menthane carboxamide and trimethyl isopropyl butanamide. Sensates may be utilized at levels of from about 0.001% to about 10%, or from about 0.005% to about 5%, or from about 0.01% to about 1%, by weight, of the total composition.

Viscosity Modifier

The compositions of the present invention can also comprise viscosity modifiers as described by U.S. Pat. No. 6,627,183, Young et al. and incorporated herein by reference. Any viscosity modifier suitable for use in hair care compositions may be used herein. Generally, if present, the viscosity modifier may comprise from about 0.01% to about 10%, or from about 0.05% to about 5%, or from about 0.1% to about 3%, by weight, of the total composition. A non-limiting list of suitable viscosity modifiers can be found in the CTFA International Cosmetic Ingredient Dictionary and Handbook, 7th edition, edited by Wenninger and McEwen, (The Cosmetic, Toiletry, and Fragrance Association, Inc., Washington, D.C., 1997), herein incorporated by reference.

Other viscosity modifiers for use herein are those which form compositions whose viscosity is also sensitive to the electrolyte concentration in the aqueous phase, known hereafter as "salt sensitive viscosity modifiers". Background material on the properties of salt sensitive viscosity modifiers can be found in American Chemical Society Symposium Series (1991), Vol. 462, pp 101-120, incorporated herein by reference. Any salt sensitive viscosity modifier suitable for use in hair care compositions may be used herein.

Examples of suitable viscosity modifiers include, but are not limited to, synthetic hectorites, carboxylic anionic polymers/copolymers and carboxylic anionic cross-linked polymers/copolymers.

Polyethylene Glycol Derivatives of Glycerides

Suitable polyethylene glycol derivatives of glycerides include any polyethylene glycol derivative of glycerides which are water-soluble and which are suitable for use in a hair care composition can be used as described by U.S. Pat. No. 6,709,648, Sako et al., incorporated herein by reference. Polyethylene glycol derivatives of glycerides that may be used include PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil.

Other suitable polyethylene glycol derivatives of glycerides can be polyethylene glycol derivatives of stearic acid. For example, PEG-30 stearate, PEG40 stearate, PEG-50 stearate, PEG-75 stearate, PEG-90 stearate, PEG-100 stearate, PEG-120 stearate, and PEG-150 stearate.

Surfactants

The compositions of the present invention can comprise a surfactant or mixture of surfactants. If present, the surfactant system may be present in the compositions herein at an active level of from about 0.001% to about 30%, or from about 0.01% to about 25%, or from about 0.1% to about 20%. It should be recognized, however, that the concentration of the surfactant system may vary with the purpose the surfactants are intended to serve, the cleaning or lather performance desired, the surfactants incorporated into the surfactant system, the desired product concentration, the presence of other components in the composition, and other factors well known in the art.

Surfactant systems useful herein can comprise one or more surfactants selected from anionic surfactants, amphoteric surfactants, nonionic surfactants, cationic surfactants and mixtures thereof.

Amphoteric surfactant components useful in the present composition include those known to be useful in personal cleansing compositions, and which may contain a group that is anionic at the pH of the compositions of the present invention. The active concentration of such surfactant components in the surfactant system of the present invention ranges from about 0.001% to about 20%, or from about 0.01% to about 15%, or from about 0.1% to about 10% by weight of the surfactant system. Examples of amphoteric surfactants suitable for use in the composition herein are described in U.S. Pat. No. 5,104,646, Bolich Jr. et al. and U.S. Pat. No. 5,106,609, Bolich Jr. et al. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylamino-propane sulfonate, sodium lauroamphoacetate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL™" and described in U.S. Pat. No. 2,528,378.

Other amphoterics, sometimes classified as zwitterionics, such as betaines can also be used in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Anionic surfactants suitable for use in the present invention include alkyl sulfate, alkyl ethoxylated sulfate, or a mixture thereof. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a salt-forming cation such as ammonium, alkanolamine containing $C_1$-$C_3$ alkyl groups such as triethanolamine, and monovalent and polyvalent metals such as the alkaline and alkaline earth metals. Metals that may be used include sodium, potassium, magnesium, and calcium. The cation M, of the anionic surfactant may be chosen such that the anionic surfactant component is water soluble. Solubility of anionic surfactants, in general, will depend upon the particular anionic surfactants and cations chosen. As an aid to determining appropriate mixtures of anionic surfactants, the anionic surfactants should be chosen such that the Krafft temperature is about 15° C. or less, or about 10° C. or less, or about 0° C. or less. The anionic surfactant may also be soluble in the composition hereof.

R may have from about 10 to about 18 carbon atoms in both the alkyl and alkyl ethoxylated sulfates. The alkyl ethoxylated sulfates may be made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are may be reacted with about 1 to about 10, or from about 1 to about 4, or from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Alkyl ether sulfates may comprise a mixture of individual compounds, said mixture having an average alkyl chain length of from about 12 to about 16 carbon atoms and an average degree of ethoxylation of from about 1 to about 4 moles of ethylene oxide.

The sulfate surfactant may be comprised of a combination of ethoxylated and nonethoxylated sulfates. Alkyl sulfates can provide excellent cleaning and lather performance. Alkyl ethoxylated sulfates can provide excellent cleaning performance.

Other suitable anionic detersive surfactants include, but are not limited to water-soluble salts of organic, sulfuric acid reaction products of the general formula $[R_1—SO_3-M]$ where $R_1$ is selected from the group consisting of a straight or branched chain, saturated aliphatic hydrocarbon radical having from about 8 to about 24, or about 10 to about 18, carbon atoms; and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen. Examples of such detersive surfactants are the salts of an organic sulfuric acid reaction product of a hydrocarbon of the methane series, including iso-, neo-, and n-paraffins, having about 8 to about 24 carbon atoms, or about 10 to about 18 carbon atoms and a sulfonating agent, e.g., $SO_3$, $H_2SO_4$, obtained according to known sulfonation methods, including bleaching and hydrolysis. Alkali metal and ammonium sulfonated $C_{10-18}$ n-paraffins may be used.

Another class of anionic surfactants suitable for use in the present invention are the reaction products of fatty acids esterified with isethionic acid and neutralized with sodium hydroxide where, for example, the fatty acids are derived from coconut oil or palm kernal oil; sodium, ammonium, tetraethylammonium or potassium salts of fatty acid amides of methyl tauride in which the fatty acids, for example, are derived from coconut oil or palm kernal oil. Other similar anionic surfactants are described in U.S. Pat. No. 2,486,921; U.S. Pat. No. 2,486,922; and U.S. Pat. No. 2,396,278.

Other anionic detersive surfactants suitable for use in the present invention are the succinnates, examples of which include disodium N-octadecylsulfosuccinate; disodium lauryl sulfosuccinate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic surfactants include alkyl glyceryl ether sulfonate surfactants (also referred to herein as an "AGS" surfactant), derivatives thereof and salts thereof. These AGS surfactants are derived from an alkyl glyceryl ether containing a sulfonate or sulfonate salt group. These compounds generally can be described as an alkyl monoether of glycerol that also contains a sulfonate group.

Cationic surfactants useful in compositions of the present invention, may contain amino or quaternary ammonium moieties. The cationic surfactant may be insoluble in the compositions hereof. Cationic surfactants among those useful herein are disclosed in the following documents, all incorporated by reference herein: M.C. Publishing Co., McCutcheon's, Detergents & Emulsifiers, (North American edition 1979); Schwartz, et al.; Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Fatty Alcohols

The hair care compositions of the present invention may also comprise fatty alcohols. Any fatty alcohol suitable for use in hair care may be used herein.

Fatty alcohols may be utilized at levels of from about 0.1% to about 20%, or from about 0.25% to about 10%, or from about 0.5% to about 5%, by weight of the composition.

If both fatty alcohol and cationic surfactant are present the ratio of alcohol:surfactant may be in the range of from about 3:1 to about 6:1, or about 4:1.

Suspending Agents

In another embodiment, the hair treatment composition, for example if it is a shampoo composition, further comprises from 0.1 to 5.0 wt % of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate may be used. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol™ materials are available from Goodrich.

Suitable cross-linked polymers of acrylic acid and acrylate esters are Pemulen TR1 or Pemulen TR2. A suitable heteropolysaccharide gum is xanthan gum.

Styling Polymers

If the product is a styling product a styling polymer may be present

The hair styling polymer if present is in the compositions of the invention in an amount of from about 0.001% to about 10% by weight, or from about 0.1% to about 10% by weight, or from about 1% to about 8% by weight.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Carriers

Hair care compositions of the present invention can comprise a carrier, or a mixture of such carriers, which are suitable for application to the hair. The carriers are present at from about 0.5% to about 99.5%, or from about 5.0% to about 99.5%, or from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Buffers or pH adjusters that may be used include weak acids and bases such glycine/sodium hydroxide, citric acid, lactic acid, succinic acid, acetic salt and salts thereof. Frequently a mixture of buffering system is used such as sodium citrate and citric acid.

Carriers suitable for use with hair care compositions of the present invention include, for example, those used in the formulation of hair sprays, mousses, tonics, gels, shampoos, conditioners, and rinses. The choice of appropriate carrier will depend on the particular product to be formulated. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse possible solvents include water, ethanol, volatile silicone derivatives, and mixtures thereof. The solvents used in such mixtures may be miscible or immiscible with each other. Mousses and aerosol hair sprays can also utilize any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilize an emulsifying agent. Examples of suitable emulsifying agents include nonionic, cationic, anionic surfactants, or mixtures thereof. If such an emulsifying agent is used, it may be present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling creams or gels also typically contain a structurant or thickener, typically in an amount of from about 0.01% to about 10% by weight.

Suitable spray containers are well known in the art and include conventional, non-aerosol pump sprays i.e., "atomizers," aerosol containers or cans having propellant, as described above, and also pump aerosol containers utilizing compressed air as the propellant.

Where the hair care compositions are conditioners and rinses, the carrier can include a wide variety of conditioning materials such as cationic conditioners suitable for hair, quaternary silicone polymers, silicone based conditioners and their emulsions, and amino functional silicones and their emulsions.

Where the hair care compositions are shampoos, the carrier can include, for example, anionic surfactants, nonionic surfactants, amphoteric surfactants, suspending agents, and thickeners Further general ingredients suitable for all product forms include, sun-screening agents, anti-dandruff actives, carboxylic acid polymer thickeners for hair shampoo and conditioner compositions and emulsifiers for emulsifying the various carrier components of the compositions of the invention.

Adjuvants

The compositions of the present invention may also contain adjuvants suitable for hair care. Generally such ingredients are included individually at a level of up to about 2, or up to about 1 wt % of the total composition. Suitable hair care adjuvants, include amino acids and ceramides.

Water

The compositions of the present invention will also generally contain water. When present water will generally comprise from about 25% to about 99%, or from about 50% to about 98%, or from about 65% to about 95%, by weight, of the total composition.

Additional Components

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other hair conditioning ingredients such as panthenol, panthetine, pantotheine, panthenyl ethyl ether, and combinations thereof, other solvents such as hexylene glycol; hair-hold polymers such as those described in WO-A-94/08557, herein incorporated by reference; detersive surfactants such as anionic, nonionic, amphoteric, and zwitterionic surfactants; additional viscosity modifiers and suspending agents such as xanthan gum, guar gum, hydroxyethyl cellulose, triethanolamine, methyl cellulose, starch and starch derivatives; viscosity modifiers such as methanolamides of long chain fatty acids such as cocomonoethanol amide; crystalline suspending agents; pearlescent aids such as ethylene glycol distearate; opacifiers such as polystyrene; preservatives such as phenoxyethanol, benzyl alcohol, methylparaben, propylparaben, imidazolidinyl urea and the hydantoins; polyvinyl alcohol; ethyl alcohol; pH adjusting agents, such as lactic acid, citric acid, sodium citrate, succinic acid, phosphoric acid, sodium hydroxide, sodium carbonate; salts, in general, such as potassium acetate and sodium chloride; colouring agents, such as any of the FD&C or D&C dyes; hair oxidising (bleaching) agents, such as hydrogen peroxide, perborate and persulfate salts; hair reducing agents, such as the thioglycolates; perfumes; sequestering agents, such as tetrasodium ethylenediamine tetra-acetate; anti-dandruff agents such as zinc pyrithione (ZPT), sulfur, selenium sulfide, coal tar, piroctone olamine, ketoconazole, climbazole, salicylic acid; antioxidants/ultra violet filtering agents such as octyl methoxycinnamate, benzophenone-3 and DL-alpha tocopherol acetate and polymer plasticizing agents, such as glycerine, diisobutyl adipate, butyl stearate, and propylene glycol. Such optional ingredients generally are used individually at levels from about 0.001% to about 10.0%, or from about 0.01% to about 5.0% by weight of the composition. pH-adjusting agents, as described above, may also be used.

Product Forms

The hair care compositions of the present invention can be formulated in a wide variety of product forms, including but not limited to creams, gels, aerosol or non-aerosol foams, mousses and sprays. Mousses, foams and sprays can be formulated with propellants such as propane, butane, pentane, dimethylether, hydrofluorocarbon, or without specifically added propellants (using air as the propellant in a pump spray or pump foamer package).

Method of Use

The hair care compositions of the present invention may be used in a conventional manner for care of human hair. An effective amount of the composition, typically from about 1 gram to about 50 grams, or from about 1 gram to about 20 grams, is applied to the hair. Application of the composition typically includes working the composition through the hair, generally with the hands and fingers, or with a suitable implement such as a comb or brush, to ensure good coverage. The composition is then left on the hair, generally until the consumer next washes their hair.

The hair may be treated using a method comprising the steps of: (a) applying an effective amount of the hair care composition to wet, damp or dry hair, (b) working the hair care composition into the hair with hands and fingers or with a suitable implement.

The method can, optionally, comprises a further step of rinsing the hair with water.

EXAMPLES

The following non-limiting examples further describe and demonstrate embodiments within the scope of the present invention. The examples are give solely for the purpose of illustration and are not to be construed as limitations of the present invention, since many variations thereof are possible without departing from the spirit and scope of the invention.

Example 1

Hair Care Composition

All ingredients are expressed on a weight percentage of the active ingredient.

| Ingredient (% wt) | Spray |
|---|---|
| Meta Silicate | 0.31 |
| Sodium Carbonate | 0.22 |
| Sodium Glyconate | 0.09 |
| Potassium Al Sulfate | 0.09 |
| Trisodium citrate | 0.7 |
| PEG 60 hydrogenated Caster oil | 0.80 |
| Lactic acid | 0.1 |
| Phenoxyethanol | 0.2 |
| Acid blue 1 | 0.0001 |
| perfume | 0.1 |
| Water | Up to 100% |

Example 21

Hair Care Composition

All ingredients are expressed on a weight percentage of the active ingredient.

| Ingredient (% wt) | Mousse |
|---|---|
| Meta Silicate | 0.31 |
| Sodium Carbonate | 0.22 |
| Sodium Glyconate | 0.09 |
| Potassium Al Sulfate | 0.09 |
| Trisodium citrate | 0.1 |
| PEG 60 hydrogenated Caster oil | 0.10 |
| CAPB (Tegobetaine F supplied by Goldschmidt) | 0.3 |
| Phenoxyethanol | 0.3 |
| Lactic Acid | 0.02 |
| perfume | 0.25 |
| Water | Up to 100% |

Hair Coloring and Bleaching Products

In a further embodiment the compositions of the invention are in the form of hair colorants, hair bleaches and/or hair tinting compositions and comprise one or more substances selected from direct dyes, oxidation dye precursors, and bleaching agents. In these compositions the composition is used in the usual pH ranges.

Suitable direct dyes include nitroaniline derivatives, such as 1-[(2-hydroxyethyl)amino]-2-nitrobenzene (Velsol® Yellow 2), 4-hydroxypropylamino-3-nitrophenol (Velsol® Red BN), 3-nitro-p-hydroxyethylaminophenol (Velsol® Red 54), 4-hydroxyethylamino-3-nitroaniline (Velsol® Red 3), N,N'-bis(hydroxyethyl)-2-nitro-p-phenylenediamine (Velsol®& Violet BS), N,N',N'-tris(hydroxyethyl)-2-nitro-p-phenylenediamine (Velsol® Blue 2), 4-(2'-hydroxyethyl)amino-3-nitrotoluene, 4-(2'-hydroxyethyl)amino-3-nitrobenzyl alcohol, 4-(2'-hydroxyethyl)amino-3-nitro-1-trifluoromethylbenzene, 4-(2',3'-dihydroxypropyl)amino-3-nitrochlorobenzene, 4-(2'-hydroxyethyl)amino-3-nitrobromobenzene, and 4-(2',3'-dihydroxypropyl)amino-3-nitrobromobenzene, nitrobenzene derivatives, for example 2-amino-4-nitrophenol, picramic acid, 1-[(2'-hydroxyethyl)amino]-2-amino-4-nitrobenzene, 2-nitro-4-[(2'-hydroxyethyl)amino]aniline, 4-bis[(2'-hydroxyethyl)amino]-1-methylamino-2-nitrobenzene, 2,5-bis[(2'-hydroxyethyl)amino]nitrobenzene, 2-(2'-hydroxyethyl)amino-4,6-dinitrophenol, 1-amino-4-(2',3'-dihydroxypropyl)amino-2-nitro-5-chlorobenzene, and also triphenylmethane dyes, such as Basic Violet 1 (C.I. 42535), azo dyes, such as Acid Brown 4 (C.I. 14805), anthraquinone dyes, such as Disperse Blue 23 (C.I. 61545), Disperse Violet 4 (C.I. 61105), 1,4,5,8-tetraminoanthraquinone and 1,4-diaminoanthraquinone and further direct dyes.

Oxidation dye precursors available are p-phenylenediamines and p-aminophenols or derivatives thereof such as p-tolylenediamine, p-phenylenediamine, and p-aminophenol, for example, which for the purpose of shading the dyeing are combined with modifiers or couplers, such as m-phenylenediamine, resorcinol, m-aminophenol and derivatives thereof.

Suitable oxidizing agents for developing the hair dyeings, or as bleaching agents, are, for example, hydrogen peroxide and its addition compounds. The composition may also be in the form of a hair bleach and comprise one or more oxidizing agents, for example, hydrogen peroxide.

To increase the color intensity, the compositions of the invention may comprise the carriers which are customary in cosmetic systems, such as benzyl alcohol, vanillin (4-hydroxy-3-methoxybenzaldehyde), isovanillin, p-hydroxyanisole, 3-hydroxy-4-methoxybenzaldehyde, 2-phenoxyethanol, salicylaldehyde, 3,5-dihydroxy-benzaldehyde, 3,4-dihydroxybenzaldehyde, 4-hydroxyphenylacetamide, methyl p-hydroxybenzoate, p-hydroxybenzaldehyde, m-cresol, hydroquinone monomethyl ether, o-fluorophenol, m-fluorophenol, p-fluorophenol, 2-(2-hydroxyphenoxy) ethanol, 3,4-methylenedioxyphenol, resorcinol monomethyl ether, 3,4-dimethoxyphenol, 3-trifluoromethylphenol, resorcinol monoacetate, ethylvanillin, 2-thiopheneethanol, butyl lactate and butyl glycolate.

The hair colorants of the invention may comprise compounds which impart pearlescence, examples being fatty acid monoalkanolamides, fatty acid dialkanolamides, mono esters or diesters of alkylene glycol, ethylene glycol and/or propylene glycol or its oligomers with higher fatty acids, e.g., palmitic acid, stearic acid or behenic acid or mixtures thereof, monoesters or diesters of alkylene glycols with fatty acids, fatty acids and their metal salts, monoesters or polyesters of glycerol with carboxylic acids, and keto sulfones of various kind, such as ethylene glycol distearate and polyethylene glycol distearate with about 3 glycol units.

Contact Lens Treatment

The liquid formulation for contact lenses of the present invention comprises one or more metasilicate; one or more carbonate; one or more glyconate; and one or more sulfate. In one embodiment, the composition comprises Meta Silicate from about 0.08% to about 3.2%, sodium carbonate from about 0.03% to about 1.2%, sodium glyconate from about 0.02% to about 0.08% and potassium Al sulfate from about 0.02% to about 0.08%. In another embodiment, the composition comprises Meta Silicate from about 0.16% to about 6.4%, sodium carbonate from about 0.06% to about 2.4%, sodium glyconate from about 0.04% to about 0.16% and potassium Al sulfate from about 0.04% to about 0.16%.

Generally known nitrogen-containing organic anti-microbial agents may be combined with the present invention when used as a contact lens treatment. Examples of the nitrogen-containing organic anti-microbial agent include polyhexamethylene biguanide, polyhexamethylene biguanide salt and quaternary ammonium salt. In the present invention, these nitrogen-containing organic anti-microbial agents may be used alone or in combination of two or more.

The liquid formulation for contact lenses of the present invention may further contain water and at least one component selected from the group consisting of buffer, surfactant, viscosity inducing agent and isotonic agent.

The buffer which can be contained in the liquid formulation for contact lenses of the present invention is not particularly limited if it is a buffer which is generally used as the formulation for contact lenses. Examples of the buffer include boric acid-based buffers and phosphoric acid-based buffers.

The surfactant that can be contained in the contact lens solutions of the present invention can be ampholytic surfactant, cationic surfactant, anionic surfactant and nonionic surfactant. Examples of the nonionic surfactant include polyoxyethylene-polyoxypropylene block copolymer, polyoxyethylene alkyl ethers, polyoxyethylene alkylphenylethers, polyoxyethylene sorbitan alkylate, polyoxyethylene hydrogenated castor oil, monoglyceryl esters of fatty acids, propylene glycol esters of fatty acids, sucrose esters of fatty acids, polyoxyethylene-polyoxypropylene ethylenediamine condensates and the like. Examples of the cationic surfactant include tri(polyoxyethylene)stearylammonium chloride (5E.O.), oleylbis(2-hydroxyethyl)methylammonium chloride, N(N'-lanolin fatty acid amide propyl)N-ethyl-N,N-dimethylammonium ethyl sulfate, N-cocoyl-L-arginineethyl ester-DL-pyrrolidonecarboxylates and the like. Examples of the ampholytic surfactant include sodium lauryl diaminoethyl glycinate, 2-alkyl-N-carboxymethyl-N-hydroxyethyl imidazolinium betain, alkyldimethylamine oxide and the like. Examples of the anionic surfactant include .alpha.-olefin sulfonates, alkyl sulfonates, alkylbenzene sulfonates, polyoxyethylene carboxylated ether salts, alkyl phosphates, polyoxyethylene alkyl ether phosphates/sulfates, alkyl sulfates, alkyl ether sulfates, alkyl sarcosinates, alkyl methyl taurine, alkylbenzene sarcosinates and the like. In the present invention, the surfactant may be used alone or in combination of two or more. When nonionic surfactant is used from among the above surfactant, it is contained in the formulation in an amount of $1 \times 10^{-4}$ to $5$ (w/v) %, or $1 \times 10^{-3}$ to $2$ (w/v) %, or $1 \times 10^{-3}$ to $1$ (w/v) %. When another surfactant is used, after an effect obtained when it is used in combination with polylysine and nitrogen-containing organic anti-microbial agent is confirmed in advance, it may be suitably used in limits that do not affect the effect.

The viscosity-inducing agent that can be contained in the liquid formulation for contact lenses of the present invention is not particularly limited if it is generally used as the formulation for opthalmology. Examples of the viscosity inducing agent include hyaluronic acid and/or salt thereof, cellulose typified by hydroxypropylmethyl cellulose, and/or derivatives thereof, chitosan and/or derivatives thereof, polyvinylpyrrolidone, polyvinyl alcohols, chondroitin sulfuric acid and salt thereof and the like. In the present invention, the above viscosity inducing agents may be used alone or in combination of two or more. The viscosity inducing agent is contained in the formulation in an amount of $1 \times 10^{-3}$ to 5 (W/V) %, or $3 \times 10^{-3}$ to 2.5 (w/v) %, or $5 \times 10^{-3}$ to $1$ (w/v) %.

The isotonic agent that can be contained in the liquid formulation for contact lenses of the present invention is not particularly limited if it is generally used as the formulation for contact lenses. Examples of the isotonic agent include sodium chloride, potassium chloride, potassium iodide, glycerin, propylene glycol, polyethylene glycol, mannitol, sorbitol, dextrin, dextran and the like. In the present invention, the above isotonic agents may be used alone or in combination of two or more.

The liquid formulation for contact lenses of the present invention may optionally contain metal chelating agent such as ethylenediamine tetraacetic acid (EDTA), citric acid, gluconic acid, tartaric acid, diethylenediamine pentaacetic acid, sodium or potassium salt thereof, and sodium nitrilotriacetate, a proteolytic enzyme derived from an animal, plant, or microorganism, and a pH adjusting agent such as hydrochloric acid and sodium hydroxide besides the above components. The liquid formulation for contact lenses of the present invention may contain at least one metal chelating agent, at least one proteolytic enzyme and at least one pH adjustor.

The pH of the liquid formulation for contact lenses of the present invention is adjusted to a range of about 5.5 to about 8.0, or about 6.8 to about 7.8 by using the appropriate pH adjusting agents. The osmotic pressure of the liquid formulation is suitably selected from a range of 180 to 460 mOsm, or 260 to 360 mOsm.

The liquid formulation for contact lenses of the present invention is a liquid formulation obtained by dissolving the above components in a solvent that is harmless to eyes, such as purified water.

The liquid formulation for contact lenses of the present invention can be advantageously produced on an industrial scale, for example, by dissolving the above components excluding viscosity inducing agent in water, adjusting the pH of the obtained solution with acid or alkali, adding viscosity inducing agent, dissolving it under stirring and adjusting the pH of the obtained solution with acid or alkali.

To clean, disinfect and store contact lenses using the liquid formulation for contact lenses of the present invention, the contact lenses taken off from eyes are soaked in the liquid formulation without cleaning by digital rubbing and left as they are for about 5 minutes to about 24 hours, or about 30 minutes to about 8 hours. Thereafter, the thus treated contact lenses can be worn in eyes without being rinsed with the liquid formulation. Although cleaning by digital rubbing which is generally necessary when MPS is used is not necessary in this method, when the contact lenses are very dirty, after they are taken off from eyes, they may be rinsed or cleaned by digital rubbing before they are soaked in the liquid formulation. When the liquid formulation is used as soaking liquid, after the contact lenses are cleaned with a commercially available general cleaning liquid or the like, they are soaked in the liquid formulation for 5 minutes or more and worn in eyes without being rinsed with the liquid formulation.

The contact lenses to be cleaned, disinfected and stored may be hard contact lenses and soft contact lenses.

Oral Care Compositions

The present invention also relates to an oral care composition. The present composition is useful for inhibiting the growth of microbials that are correlated to the formation of biofilm in the oral cavity. It is believed that plaque and eventually tartar and calculus result from a biofilm reaching a more advanced and complex stage of development, trapping additional material and eventually hardening. Therefore, by inhibiting the development of the biofilm, the development of plaque tartar and/or calculus may also be prevented.

In this embodiment, the composition comprises meta silicate, carbonate glyconate, and aluminum sulfate in a suitable carrier for the treatment of oral cavities and teeth. The composition may comprise a) from about 0.08% to about 3.2% of a meta silicate, b) from about 0.06% to about 2.4% of a carbonate, c) from about 0.02% to about 0.08% of a glyconate, and d) from about 0.02% to about 0.08% of a sulfate. The concentration used for oral care products is about 1.5 to about 2 times that of the concentration used for skincare products or shampoos due to the less sensitive inner mouth skin composition and the needed direct effect of the toothpaste and mouth water. The composition is delivered to the oral cavity or teeth using a suitable carrier as described below.

In this embodiment, compositions may include additional active ingredients that improve oral hygiene or the appearance of the teeth. In addition, agents that improve aesthetics or efficacy of the product may also be used and are described herein.

Additional Ingredients

Essential Oils

In another embodiment, the present invention can incorporate essential oils demonstrating antimicrobial properties as described in U.S. Application 20060045851, Oral care composition comprising essential oils, Fitzgerald et al., published Mar. 2, 2006.

Oral Care Carriers

The oral care composition comprising the combination of Group A and B essential oils can also comprise a variety of oral care carriers including dentifrice, rinse, gel, gum, candy, confectionary or lozenge, edible film, and/or a quick dissolving wafer such as described in U.S. Pat. No. 6,221,392. Additionally, the oral care composition can be disposed on a dental wipe such as described in U.S. Pat. No. 6,721,987 and WO Application No. 02/069753.

The choice of a carrier to be used is determined by the way the composition is to be introduced into the oral cavity. If a tooth paste (including tooth gels, chewable tablets etc.) is to be used, then a "toothpaste carrier" is chosen as disclosed in, e.g., U.S. Pat. No. 3,988,433, (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 (e.g., water, flavoring and sweetening agents, etc.). Similarly, if a mouth spray is to be used, then a "mouth spray carrier" is chosen. If a sachet is to be used, then a "sachet carrier" is chosen (e.g., sachet bags flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos.

5,198,220; and 5,242,910. Carriers suitable for the preparation of compositions of the present invention are well known in the art. Their selection will depend on secondary considerations like taste, cost, and shelf stability, etc.

In one embodiment of the subject invention, the compositions are in the form of dentifrices, such as toothpastes, tooth gels and tooth powders. Components of such toothpaste and tooth gels may include one or more of a dental abrasive (from about 10% to about 50%), a surfactant (from about 0.5% to about 10%), a thickening agent (from about 0.1% to about 5%), a humectant (from about 10% to about 55%), an essential oil component (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an additional anticaries agent (from about 0.05% to about 10% additional anticaries agent), and an anticalculus agent (from about 0.1% to about 13%). The tooth powders, of course, contain substantially all non-liquid components.

Other embodiments of the compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an of additional anticaries agent (from about 0.05% to about of additional anticaries agent), and an anticalculus agent (from about 0.1% to about 13%).

Other embodiments of the compositions of the subject invention are dental solutions. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Another embodiment of the present invention includes a candy, confection and/or lozenge. The carrier material for the candy, confection and/or lozenge can be chosen from chewable or non chewable materials. The chewable material can be selected from gums including, but not limited to, agar gum, and gelatine; low boiled sugar candy base and gum base materials. Hard and low boiled candy carrier, pressed tablets and the like can comprise greater than about 70% bulk sweetener including suitable sugar and sugar syrups including cariogenic and non-cariogenic materials. Low boiled candies can also comprise butter to form chewable toffee. For jelly and gum drop compositions the carrier can comprise greater than about 25% bulk sweetener and additionally comprise gums including gum arabic, gelatine, agar powder and the like. In addition to the essential oil composition, the candy, confections and/or lozenge can additionally comprise other oral and/or therapeutic actives.

Another embodiment of the present invention includes chewing gum compositions. Such compositions may be in the form of a conventional chewing gum or any other product form which is suitable for chewing. Suitable physical forms include sticks, dragees, chiclets, and batons. A chewing gum is typically retained in the oral cavity for a time sufficient to allow ingredients released to contact substantially all of the dental surfaces and/or oral tissues for purposes of oral activity. Chewing gums can comprise abrasive polishing materials, elastomers, resins, plasticizers, fats, solvents, bulking agents, sweeteners, absorbents, orally active metallic ions, cationic material, fluoride ion sources, additional anticalculus agents, antimicrobial agents, buffers, whitening agents, alkali metal bicarbonate salts, thickening materials, humectants, water, surfactants, titanium dioxide, flavoring agents, xylitol, coloring agents, and mixtures thereof.

In another embodiment of the present invention, the essential oil composition is present in an edible film that is physiologically acceptable and particularly well adapted to adhere to and dissolve in the oral cavity of a consumer. Examples of suitable edible film and methods for making such films are described in U.S. Pat. Nos. 6,596,298; 5,733,584; 5,948,430; 6,177,096; and W.O. Application No. 00/18365. An edible film comprising pullulan can be used. The edible films of the present invention can be used to deliver or release the essential oil composition and/or other oral care active. The edible films can include a variety of other suitable ingredients such as softeners, colorants, flavoring agents, emulsifiers, surfactants, thickening agents, binding agents, sweeteners, fragrances, and combinations thereof.

The compositions of the present invention can further comprise abrasives, surfactants, thickening agents, humectants and flavorants previously disclosed it the art.

Abrasives

In another embodiment of the present invention a dental abrasive may be included. The material selected is to be compatible within the composition of interest and does not excessively abrade dentin. Suitable abrasives include, for example silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types can be used because of their unique benefits of exceptional dental cleaning and polishing performance without unduly abrading tooth enamel or dentine. The silica abrasive polishing materials can have an average particle size ranging between about 0.1 to about 30 microns, and in another embodiment from about 5 to about 15 microns. The abrasive can be precipitated silica or silica gels such as the silica xerogels described in U.S. Pat. No. 3,538,230, and U.S. Pat. No. 3,862,307. Suitable silica xerogels are the silica xerogels marketed under the trade name "Syloid" by the W.R. Grace & Company, Davison Chemical Division. Also precipitated silica materials, such as those marketed by the J. M. Huber Corporation under the trade name, Zeodent®, can be used; in one embodiment the silica carrying the designation Zeodent 119® can be used. The types of silica dental abrasives useful in the toothpastes of the present invention are described in more detail in U.S. Pat. No. 4,340,583. The abrasive in the toothpaste compositions described herein is generally present at a level of from about 6% to about 70% by weight of the composition. The toothpastes can contain from about 10% to about 50% of abrasive, by weight of the composition. Mixtures of the abrasives can be used. Examples of suitable precipitated silica is the silica disclosed in U.S. Pat. Nos. 5,603,920; 5,589,160; 5,658,553; 5,651,958.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures-thereof. Many suitable-nonionic and amphoteric surfactants are disclosed in U.S. Pat. Nos. 3,988,433; and 4,051,234, and many suitable nonionic surfactants are disclosed in U.S. Pat. No. 3,959,458, Thickening Agents In preparing toothpaste or gels, it is necessary to add some thickening material to provide a desirable consistency of the composition, to provide desirable release characteristics upon use, to provide shelf stability, and to provide stability of the composition, etc. Suitable thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Thickening agents can include however, except polymeric polyether compounds, e.g., polyethylene or polypropylene oxide (M.W. 300 to 1,000,000), capped with alkyl or acyl groups containing 1 to about 18 carbon atoms.

A suitable class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly the carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220; 5,242,910; and 4,443,430.

Thickening agents in an amount from about 0.1% to about 15%, or from about 0.2% to about 6%, in another embodiment from about 0.4% to about 5%, by weight of the total toothpaste or gel composition, can be used. Higher concentrations can be used for non-abrasive gels and subgingival gels.

Humectants

Another optional component of the topical, oral-carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, can comprise from about 0% to about 70%, and in another embodiment from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Sweetening Agents

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition can contain from about 0.1% to about 10% of these agents, in another embodiment from about 0.1% to about 1%, by weight of the composition.

In addition to sweetening agents, coolants, salivating agents, warming agents, and numbing agents can be used as optional ingredients in compositions of the present invention. These agents are present in the compositions at a level of from about 0.001% to about 10%, in another embodiment from about 0.1% to about 1%, by weight of the composition.

The coolant can be any of a wide variety of materials. Included among such materials are carboxamides, menthol, ketals, diols, and mixtures thereof. Suitable coolants in the present compositions include the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro and a levorotatory isomers of these compounds and racemic mixtures thereof. TK10 is described in U.S. Pat. No. 4,459,425. WS-3 and other agents are described in U.S. Pat. No. 4,136,163.

Suitable salivating agents of the present invention include Jambu® manufactured by Takasago. Suitable warming agents include *capsicum* and nicotinate esters, such as benzyl nicotinate. Suitable numbing agents include benzocaine, lidocaine, clove bud oil, and ethanol.

Cosmetic or Therapeutic Actives

The oral care composition may also comprise suitable cosmetic and/or therapeutic actives. Such actives include any material that is generally considered safe for use in the oral cavity and that provides changes to the overall appearance and/or health of the oral cavity, including, but not limited to, anti-calculus agents, fluoride ion sources, stannous ion sources, whitening agents, anti-microbial, anti-plaque agents, anti-inflammatory agents, nutrients, antioxidants, anti-viral agents, analgesic and anesthetic agents, H-2 antagonists, components which impart a clean feel to the teeth, pigments and colorants, fragrances and sensates, and mixture thereof. When present, the level of cosmetic and/or therapeutic active in the composition is, in one embodiment from about 0.001% to about 90%, in another embodiment from about 0.01% to about 50%, and in another embodiment from about 0.1% to about 30%, by weight of the composition.

The following is a non-limiting list of actives that may be used in the present invention.

Anticalculus Agent

Compositions of the present invention may also comprise an anti-calculus agent, which in one embodiment may be present from about 0.05% to about 50%, by weight of the oral care composition, in another embodiment is from about 0.05% to about 25%, and in another embodiment is from about 0.1% to about 15%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof, polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≅6), Hexaphos (n≅3), and Glass H (n≅21, sodium hexametaphosphate), and mixtures thereof. The pyrophosphate salts useful in the present invention include, alkali metal pyrophosphates, di-, tri-, and monopotassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Stannous Ion

The oral care compositions of the present invention may include a stannous ion source. The stannous ions may be provided from stannous fluoride and/or other stannous salts. Stannous fluoride has been found to help in the reduction of gingivitis, plaque, sensitivity, and in improved breath benefits. The stannous ions provided in an oral composition will provide efficacy to a subject using the composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 3,000 ppm to about 15,000 ppm stannous ions in the total composition. The stannous ion is present in an amount of from about 4,000 ppm to about 12,000 ppm, in one embodiment from about 5,000 ppm to about 10,000 ppm. Other stannous salts include organic stannous carboxylates, such as stannous acetate, stannous gluconate, stannous oxalate, stannous malonate, stannous citrate, stannous ethylene glycoxide, stannous formate stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.001% to about 11%, by weight of the compositions. The stannous salts may, in one embodiment, be present in an amount of from about 0.01% to about 7%, in another embodiment from about 0.1% to about 5%, and in another embodiment from about 1.5% to about 3%, by weight of the composition.

Whitening Agent

A whitening agent may also be included in the present compositions. The actives suitable for whitening are selected from the group consisting of alkali metal and alkaline earth metal peroxides, metal chlorites, perborates inclusive of mono and tetrahydrates, perphosphates, percarbonates, peroxyacids, and persulfates, such as ammonium, potassium, sodium and lithium persulfates, and combinations thereof. Suitable peroxide compounds include hydrogen peroxide, urea peroxide, calcium peroxide, carbamide peroxide, magnesium peroxide, zinc peroxide, strontium peroxide and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine, respectively, that the molecule is capable of providing to bleach the stain. In one embodiment the whitening agents may be present at levels from about 0.01% to about 40%, in another embodiment from about 0.1% to about 20%, in another embodiment form about 0.5% to about 10%, and in another embodiment from about 4% to about 7%, by weight of the composition.

Anti-Microbial Agent

Anti-microbial agents may be included in the compositions of the present invention. Such agents may include, but are not limited to: 5-chloro-2-(2,4-dichlorophenoxy)-phenol, commonly referred to as triclosan; 8-hydroxyquinoline and its salts; copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, including magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; niacin preparations; zinc or stannous ion agents; nystatin; grapefruit extract; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; and mixtures of all of the above. Anti-microbial components may be present from about 0.001% to about 20% by weight of the composition.

Anti-Plaque Agent

The compositions of the present invention may include an anti-plaque agent such as stannous salts, copper salts, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol in one embodiment can be present in a level of from about 0.001% to about 25%, in another embodiment from about 0.01% to about 5%, and in another embodiment from about 0.1% to about 1.5% by weight of the composition.

Anti-Inflammatory Agent

Anti-inflammatory agents can also be present in the oral care compositions of the present invention. Such agents may include, but are not limited to, non-steroidal anti-inflammatory (NSAID) agents oxicams, salicylates, propionic acids, acetic acids and fenamates. Such NSAIDs include but are not limited to ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as ketorolac are claimed in U.S. Pat. No. 5,626,838. Disclosed therein are methods of preventing and/or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluocinolone, and hydrocortisone.

Nutrients

Nutrients may improve the condition of the oral cavity and can be included in the oral care compositions of the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyancobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-camitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in Drug Facts and Comparisons (loose leaf drug information service), Wolters Kluer Company, St. Louis, Mo., ©1997, pps. 3-17 and 54-57.

Antioxidants

Antioxidants are generally recognized as useful in oral care compositions. Antioxidants are disclosed in texts such as Cadenas and Packer, The Handbook of Antioxidants, ©1996 by Marcel Dekker, Inc. Antioxidants useful in the present invention include, but are not limited to, Vitamin E, ascorbic acid, Uric acid, carotenoids, Vitamin A, flavonoids and polyphenols, herbal antioxidants, melatonin, aminoindoles, lipoic acids and mixtures thereof.

Analgesic and Anesthetic Agents

Anti-pain or desensitizing agents can also be present in the oral care compositions of the present invention. Analgesics are agents that relieve pain by acting centrally to elevate pain threshold without disturbing consciousness or altering other sensory modalities. Such agents may include, but are not limited to: strontium chloride, potassium nitrate; sodium fluoride; sodium nitrate; acetanilide; phenacetin; acertophan; thiorphan; spiradoline; aspirin; codeine; thebaine; levorphenol; hydromorphone; oxymorphone; phenazocine; fentanyl; buprenorphine; butaphanol; nalbuphine; pentazocine; natural herbs, such as gall nut; Asarum; Cubebin; Galanga; scutellaria; Liangmianzhen; and Baizhi. Anesthetic agents, or topical analgesics, such as acetaminophen, sodium salicylate, trolamine salicylate, lidocaine and benzocaine may also be present. These analgesic actives are described in detail in Kirk-Othmer, Encyclopedia of Chemical Technology, Fourth Edition, Volume 2, Wiley-Interscience Publishers (1992), pp. 7, 29-737.

H-1 and H-2 Antagonists

The present invention may also optionally comprise selective H-1 and H-2 antagonists as disclosed in U.S. Pat. No. 5,294,433.

Pigments and Colorants

Pigments may be added to the compositions herein to more precisely indicate the locations at which the composition has actually been in contact. Additionally, these substances may be suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth. Where the pigment is for the satisfaction of the consumer, appropriate pigment levels are selected for the particular impact that is desirable to the consumer. The levels of pigments and colorants may be in the range of about 0.001% to about 20%, in one embodiment from about 0.01% to about 15% and in another embodiment from about 0.1% to about 10% by total weight of the chewing oral care composition.

Pigments and colorants include inorganic white pigments, inorganic colored pigments, pearling agents, filler powders and the like; see Japanese Published Patent Application Kokai No. 9 [1997]-100215, published Apr. 15, 1997. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In one embodiment the pigments and colorants are those selected from the group consisting of titanium dioxide, bismuth oxychloride, zinc oxide, Opatint D&C Red 27, CI 16185:1 Acid 27 Lake E123, C114720:1 Carmosoisine Aluminum Lake E122, Red 7 Lake, or Red 30 Lake and mixtures thereof.

Additional Active Ingredients

Additional active ingredients suitable for use in the present invention may include, but are not limited to, insulin, steroids, herbal and other plant derived remedies, and antineoplastics. Additionally, anti-gingivitis or gum care agents known in the art may also be included. Components which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single oral care composition to provide combined effectiveness.

Optional agents to be used include such known materials as synthetic anionic polymers, including polyacrylates and copolymers of maleic anhydride or acid and methyl vinyl ether (e.g., Gantrez), as described, for example, in U.S. Pat. No. 4,627,977, as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof. Additionally, the oral care composition can include a polymer carrier, such as those described in U.S. Pat. Nos. 6,682,722 and 6,589,512 and U.S. application Ser. Nos. 10/424,640 and 10/430,617.

Alkali Metal Bicarbonate Salt

The present invention may also include an alkali metal bicarbonate salt. Alkali metal bicarbonate salts are soluble in water and unless stabilized, tend to release carbon dioxide in an aqueous system. In one embodiment sodium bicarbonate, also known as baking soda, is the alkali metal bicarbonate salt. The present composition may contain from about 0.5% to about 30%, in another embodiment from about 0.5% to about 1.5%, and in another embodiment from about 0.5% to about 5% of an alkali metal bicarbonate salt.

Miscellaneous Carriers

Water employed in the preparation of commercially suitable oral compositions should be of low ion content and free of organic impurities. Water generally comprises from about 5% to about 70%, and in another embodiment from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Antimicrobial antiplaque agents may also be optionally present in oral compositions. Such agents may include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 34.11); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above antimicrobial antiplaque agents. If present, the antimicrobial antiplaque. agents generally comprise from about 0.1% to about –5% by-weight-of the-compositions of the present invention.

Other optional agents include synthetic anionic polymeric polycarboxylates being employed in the form of their free acids or partially or fully neutralized water soluble alkali metal (e.g. potassium and sodium) or ammonium salts and are disclosed in U.S. Pat. Nos. 4,152,420; 3,956,480; 4,138,477; 4,183,914; and 4,906,456. In one embodiment the copolymers can be 1:4 to 4:1 copolymers of maleic anhydride or acid with another polymerizable ethylenically unsaturated monomer, in particular the methyl vinyl ether (methoxyethylene) can have a molecular weight (M.W.) of about 30,000 to about 1,000,000. These copolymers are available for example as Gantrez (AN 139 (M.W. 500,000), A.N. 119 (M.W. 250,000) and as S-97 Pharmaceutical Grade (M.W. 70,000), of GAF Corporation.

Methods of Use

A safe and effective amount of the compositions of the present invention may be topically applied to the mucosal tissue of the oral cavity, to the gingival tissue of the oral cavity, and/or to the surface of the teeth, for the treatment or prevention of biofilms or bacterial growth, in several conventional ways. For example, the gingival or mucosal tissue may be rinsed with a solution (e.g., mouth rinse, mouth spray); or in a dentifrice (e.g., toothpaste, tooth gel, chewable tablet, tooth powder), the gingival/mucosal tissue and/or teeth are bathed in the liquid and/or lather generated by brushing the teeth. A chewable dentifrice tablet can be chewed thus delivering the tooth actives to the surfaces of the oral cavity such as described in U.S. patent application Publication Nos. 2004/0101493 and 2004/0101494. The teeth can then be brushed after the tablet is chewed. Other non-limiting examples include applying a non-abrasive gelpor paste, directly to the gingival/mucosal tissue or to the teeth with or without an oral care appliance described below.

For a method of reducing the microbials correlated to the formation of biofilm in the oral cavity, a safe and effective amount of the oral care composition of the present invention can be administered to the oral cavity of a subject in need thereof. The compositions of the present invention can be applied to the gingival/mucosal tissue and/or the teeth (for example, by rinsing with a mouthrinse, directly applying a non-abrasive gel with or without a device, applying a dentifrice or a tooth gel with a toothbrush, etc.) of a person in need thereof, for at least about 10 seconds, in another embodiment from about 20 seconds to about 10 minutes, in even another embodiment from about 30 seconds to about 60 seconds. The method often involves expectoration of most of the composition following such contact. The frequency of such contact can be from about once per week to about four times per day, in another embodiment from about thrice per week to about three times per day, and in another embodiment from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity. The period of such treatment typically ranges from about one day to a lifetime. The subject may repeat the application as needed. The duration of treatment can be from about 3 weeks to about 3 months, but may be shorter or longer depending on the severity of the condition being treated, the particular delivery form utilized and the patient's response to treatment.

Additionally, the oral cavity can be treated by using edible films, candy, confectionary, lozenges and/or gums. Such compositions are retained in the oral cavity for a substantial period of time during consumption, and therefore, provide an ideal product form for a portable oral care product.

The compositions of this invention are useful for both human and other lower animal (e.g. pets, zoo, or domestic animals) applications.

What is claimed is:

1. A composition for treating the skin or scalp, comprising:
   (a) from about 0.11% to about 0.84% of one or more metasilicate;
   (b) from about 0.08% to about 0.64% of one or more carbonate;
   (c) from about 0.03% to about 0.26% of one or more glyconate; and
   (d) from about 0.03% to about 0.26% of one or more sulfate;
wherein the pH of the composition is about 5 to about 8; wherein the composition is suitable for treating the skin or scalp; wherein the sulfate comprises potassium aluminum sulfate; wherein the composition further comprises a physiologically-acceptable carrier or diluent.

2. The composition of claim 1, wherein the one or more metasilicate is an alkali metal silicate selected from the group consisting of sodium or potassium metasilicate, sodium or potassium orthosilicate and mixtures thereof.

3. The composition of claim 2, wherein the one or more carbonate is selected from the group consisting of sodium carbonate, sodium sesquicarbonate, sodium bicarbonate and mixtures thereof.

4. The composition of claim 3, wherein the glyconate is selected from the group consisting of ammonium glyconate, lithium glyconate, sodium glyconate, sodium starch glyconate, potassium glyconate, ammonium acid glyconate, sodium acid glyconate, lithium acid glyconate, potassium acid glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

5. The composition of claim 4, wherein the composition further comprises (e) one or more salts.

6. The composition of claim 5, wherein the composition further comprises an emulsifying agent, a surfactant, a thickening agent, or a mixture thereof.

7. The composition of claim 4, wherein the composition comprises a) from about 0.21% to about 0.42% of a meta silicate, b) from about 0.16% to about 0.32% of a carbonate, c) from about 0.06% to about 0.13% of a glyconate, and d) from about 0.06% to about 0.13% of a sulfate.

8. The composition of claim 5, wherein the carbonate is sodium carbonate, wherein the glyconate is sodium glyconate, and wherein the sulfate is potassium aluminum sulfate.

9. The composition of claim 1, wherein the carrier is selected from the group consisting of liposomes, solutions, creams, emollients, ointments, gels, solid formulations and liquid formulations.

10. The composition of claim 9, wherein the composition is in the form of a liquid, cream, oil, gel, fluid cream, lotion, emulsion or microemulsion.

11. The composition of claim 5, wherein the composition further comprises an active drug substance.

12. The composition of claim 11, wherein the active drug substance is a corticosteroid, metronidazole, sulfacetamide, sulfur, or azelaic acid or a combination thereof.

13. The composition of claim 10, wherein the composition further comprises an active cosmetic selected from the group consisting of desquamatory actives, anti-acne actives, retinoids, peptides, hydroxy acids, anti-oxidants, radical scavengers, chelators, anti-inflammatory agents, topical anesthetics, tanning actives, skin lightening agents, anti-cellulite agents, flavonoids, antimicrobial actives, skin soothing agents, skin healing agents, antifungal actives, sunscreen actives, conditioning agents, structuring agents, thickening agents, and mixtures thereof.

14. The composition of claim 13, wherein the active cosmetic substance is retinol, a retinol derivative, or a mixture thereof.

15. The composition of claim 13, wherein the active cosmetic substance is allantoin, retinyl propionate, tocopherol, tocopherol derivatives, tocopherol esters, peptides, peptide derivatives, niacinamide, phytosterols, isoflavones, panthenol, panthenol derivatives, salicylic acid bisabolol or farnesol.

16. The composition of claim 10, wherein the composition further comprises a skin lightening agent, a sunscreen agent, a skin conditioning agent, a skin protectant, an emollient, a humectant, or a mixture thereof.

17. The composition of claim 10, further comprising an effective amount of an active agent selected from the group consisting of psoriasis-alleviating agents, anti-microbial agents, anti-inflammatory agents and combinations thereof.

18. The composition of claim 10, further comprises a nutrient selected from the group consisting of vitamins, essential amino acids, essential fatty acids, and cosmetically acceptable salts and esters thereof.

19. The composition of claim 18, wherein the nutrient is selected from the group consisting of vitamin A, vitamin E, essential amino acids, and cosmetically acceptable salts and esters thereof.

20. The composition of claim 10, wherein the composition further comprises colorants, pigments, film-forming agents, thickening agents, shine-control agents, skin conditioning agents, humectants, exfoliants, powders, solidifying agents, spray propellants, fragrances, surfactants, sunscreen, antioxidants, chelators, skin-lightening agents, anti-aging additives, anti-septics, preservatives, anti-microbials, anesthetics, pH-adjusting agents, chaotropic agents, and combinations thereof.

21. The composition of claim 10, wherein the concentration is in an amount effective to treat skin damage.

22. A composition for treating the skin or scalp, comprising:
   a) from about 0.04% to about 1.6% of a meta silicate,
   b) from about 0.03% to about 1.2% of a carbonate,
   c) from about 0.01% to about 0.04% of a glyconate, and
   d) from about 0.01% to about 0.04% of a sulfate;

wherein the pH of the composition is about 5 to about 8; wherein the composition is suitable for treating the skin or scalp; wherein the sulfate comprises potassium aluminum sulfate.

23. A method for the treatment of skin damage comprising topically applying to the skin a composition containing an effective amount of the composition of any of claim 1-22.

24. A method according to claim 23 wherein the skin damage is selected from the group consisting of eczema, atopic dermatitis, contact dermatitis, seborrhea, xerosis, rosacea, thermal or radiation burns, wounds, and psoriasis.

25. A method according to claim 23 wherein the skin damage is inflammation or aging.

26. The composition of claim 10, wherein the composition is in the form of a shampoo, lotion or conditioner and comprises an amount effective for treating the hair, skin, or scalp.

27. The composition of claim 26, wherein the composition further comprises a conditioning agent.

28. The composition of claim 27, wherein the conditioning agent is selected from the group consisting of cationic polymers, polyolefins, hydrocarbon oils, silicone gums, silicone oils, and mixtures thereof.

29. The composition of claim 28, wherein the conditioner is present in a proportion of 0.001% to 60% by weight relative to the total weight of the composition.

30. The composition of claim 26, wherein the composition further comprises a detersive surfactant.

31. The composition of claim 30, wherein the surfactant is present in an amount of from about 10 to 90 percent by weight of the composition.

32. The composition of claim 26, wherein the composition further comprises a preservative in an amount from about 0.01 to 6 weight percent of the composition.

33. The composition of claim 26, further comprising a moisturizer.

34. The composition of claim 33, wherein the moisturizer comprises one or more of wheat protein, hair keratin amino acids, sodium peroxylinecarbolic acid, panthenol, tocopherol, or dimethicone.

35. The composition of claim 34, wherein the moisturizer is present in an amount from about 0.01 to 2 weight percent of the composition.

36. A method of treating hair or scalp comprising applying to the hair or scalp at least one composition as defined in any of claim 26-35.

37. The method of claim 36, further comprising the step of rinsing the hair or scalp with water after the applying step.

38. The method of claim 37, further comprising the step of leaving the composition on the hair for a period of time before the rinsing step.

39. The method of claim 37, wherein the composition is an aqueous solution in the form of a mousse, cream, gel, aerosol or non-aerosol spray, or lotion.

40. A method according to claim 24, wherein the a wound is the result of a skin break, muscle tear, burn, surgical procedure, infectious disease, or an underlying condition.

41. The composition of claim 1; wherein the pH of the composition is about 5 to about 7.

* * * * *